(12) United States Patent
Danitz

(10) Patent No.: US 8,182,417 B2
(45) Date of Patent: May 22, 2012

(54) ARTICULATING MECHANISM COMPONENTS AND SYSTEM FOR EASY ASSEMBLY AND DISASSEMBLY

(75) Inventor: David J. Danitz, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1677 days.

(21) Appl. No.: 11/121,668

(22) Filed: May 3, 2005

(65) Prior Publication Data

US 2006/0111616 A1    May 25, 2006

Related U.S. Application Data

(60) Provisional application No. 60/630,912, filed on Nov. 24, 2004.

(51) Int. Cl.
*A61B 1/00* (2006.01)

(52) U.S. Cl. ............. 600/141; 600/142; 606/1; 606/170

(58) Field of Classification Search .......... 600/139–141, 600/146, 149, 142; 606/129, 1, 170; 403/52, 403/72, 123; 248/49
See application file for complete search history.

(56) References Cited

U.S. PATENT DOCUMENTS

| | | | |
|---|---|---|---|
| 1,820,463 A | 8/1931 | Klein | |
| 3,060,972 A | 10/1962 | Sheldon | |
| 3,071,161 A | 1/1963 | Ulrich | |
| 3,190,286 A | 6/1965 | Stokes | |
| 3,557,780 A | 1/1971 | Sato | |
| 3,605,725 A | 9/1971 | Bentov | |
| 4,466,649 A | 8/1984 | Ozawa | |
| 4,489,826 A | 12/1984 | Dubson | |
| 4,580,551 A | 4/1986 | Siegmund et al. | |
| 4,700,693 A | 10/1987 | Lia et al. | |
| 4,763,669 A | 8/1988 | Jaeger | |
| 4,790,294 A | 12/1988 | Allred et al. | |
| 4,834,761 A | 5/1989 | Walters | |
| 4,854,626 A | 8/1989 | Duke | |
| 4,880,015 A | 11/1989 | Nierman | |
| 4,984,951 A | 1/1991 | Jameson | |
| 5,158,086 A * | 10/1992 | Brown et al. | .................. 600/459 |
| 5,174,276 A | 12/1992 | Crockard | |
| 5,257,618 A | 11/1993 | Kondo | |
| 5,271,381 A | 12/1993 | Ailinger et al. | |
| 5,273,026 A | 12/1993 | Wilk | |
| 5,286,228 A | 2/1994 | Lee et al. | |
| 5,297,443 A | 3/1994 | Wentz | |
| 5,314,424 A | 5/1994 | Nicholas | |
| 5,322,064 A | 6/1994 | Lundquist | |

(Continued)

FOREIGN PATENT DOCUMENTS

EP         0 165 718          12/1985

(Continued)

OTHER PUBLICATIONS http://engr.bd.psu.edu/pkoch/plasticdesign/snap_design.htm date verified via internet archive (Sep. 2, 2003).*

(Continued)

*Primary Examiner* — Ryan Severson
*Assistant Examiner* — David Eastwood

(57) ABSTRACT

A component-based system for assembling articulating mechanisms that generally includes a variety of link, joint, central and spacer components together with connecting cables of varying lengths.

21 Claims, 16 Drawing Sheets

U.S. PATENT DOCUMENTS

| | | | |
|---|---|---|---|
| 5,325,845 A | 7/1994 | Adair | |
| 5,330,502 A | 7/1994 | Hassler et al. | |
| 5,354,162 A | 10/1994 | Burdea et al. | |
| 5,381,782 A | 1/1995 | DeLaRama et al. | |
| 5,405,344 A | 4/1995 | Williamson et al. | |
| 5,425,743 A | 6/1995 | Nicholas | |
| 5,441,494 A | 8/1995 | Ortiz | |
| 5,454,827 A | 10/1995 | Aust et al. | |
| 5,476,479 A | 12/1995 | Green et al. | |
| 5,486,154 A | 1/1996 | Kelleher | |
| 5,490,819 A | 2/1996 | Nicholas et al. | |
| 5,498,256 A | 3/1996 | Furnish | |
| 5,513,827 A * | 5/1996 | Michelson | 248/279.1 |
| 5,520,678 A | 5/1996 | Heckele et al. | |
| 5,522,788 A | 6/1996 | Kuzmak | |
| 5,549,636 A | 8/1996 | Li | |
| 5,562,699 A | 10/1996 | Heimberger et al. | |
| 5,570,919 A | 11/1996 | Eusebe | |
| 5,599,151 A | 2/1997 | Daum et al. | |
| 5,609,601 A | 3/1997 | Kolesa et al. | |
| 5,620,415 A | 4/1997 | Lucey et al. | |
| 5,624,398 A | 4/1997 | Smith et al. | |
| 5,626,608 A | 5/1997 | Cuny et al. | |
| 5,632,432 A | 5/1997 | Schulze et al. | |
| 5,643,294 A | 7/1997 | Tovey et al. | |
| 5,647,743 A * | 7/1997 | Schmitt | 433/23 |
| 5,702,408 A | 12/1997 | Wales et al. | |
| 5,704,534 A | 1/1998 | Huitema et al. | |
| 5,713,505 A | 2/1998 | Huitema | |
| 5,716,352 A | 2/1998 | Viola et al. | |
| 5,759,151 A | 6/1998 | Sturges et al. | |
| 5,792,164 A | 8/1998 | Lakatos et al. | |
| 5,807,376 A | 9/1998 | Viola et al. | |
| 5,813,813 A | 9/1998 | Daum et al. | |
| 5,823,066 A | 10/1998 | Huitema et al. | |
| 5,827,323 A | 10/1998 | Klieman et al. | |
| 5,836,960 A | 11/1998 | Kolesa et al. | |
| 5,845,540 A | 12/1998 | Rosheim | |
| 5,846,183 A | 12/1998 | Chilcoat | |
| 5,873,817 A | 2/1999 | Kokish et al. | |
| 5,899,425 A | 5/1999 | Corey, Jr. et al. | |
| 5,916,146 A * | 6/1999 | Allotta et al. | 600/141 |
| 5,916,147 A | 6/1999 | Boury | |
| 5,921,956 A | 7/1999 | Grinberg et al. | |
| 5,938,678 A | 8/1999 | Zirps et al. | |
| 5,947,984 A | 9/1999 | Whipple | |
| 5,961,532 A | 10/1999 | Finley et al. | |
| 6,019,722 A | 2/2000 | Spence et al. | |
| 6,050,996 A | 4/2000 | Schmaltz et al. | |
| 6,161,543 A | 12/2000 | Cox et al. | |
| 6,250,532 B1 | 6/2001 | Green et al. | |
| 6,270,453 B1 | 8/2001 | Sakai | |
| 6,464,704 B2 | 10/2002 | Schmaltz et al. | |
| 6,471,641 B2 * | 10/2002 | Sakamoto | 600/142 |
| 6,471,696 B1 | 10/2002 | Berube et al. | |
| 6,482,149 B1 * | 11/2002 | Torii | 600/142 |
| 6,491,626 B1 * | 12/2002 | Stone et al. | 600/141 |
| 6,571,042 B1 | 5/2003 | Kordahi | |
| 6,626,824 B2 | 9/2003 | Ruegg et al. | |
| 6,635,071 B2 | 10/2003 | Boche et al. | |
| 6,638,213 B2 * | 10/2003 | Ogura et al. | 600/148 |
| 6,638,287 B2 | 10/2003 | Danitz et al. | |
| RE38,335 E * | 11/2003 | Aust et al. | 606/170 |
| 6,641,528 B2 * | 11/2003 | Torii | 600/142 |
| 6,644,532 B2 | 11/2003 | Green et al. | |
| 6,666,854 B1 | 12/2003 | Lange | |
| 6,669,254 B2 | 12/2003 | Thom et al. | |
| 6,676,676 B2 | 1/2004 | Danitz et al. | |
| 6,682,541 B1 | 1/2004 | Gifford et al. | |
| 6,743,239 B1 * | 6/2004 | Kuehn et al. | 606/139 |
| 6,746,443 B1 | 6/2004 | Morley et al. | |
| 6,749,560 B1 | 6/2004 | Konstorum et al. | |
| 6,752,823 B2 | 6/2004 | Prestel | |
| 6,764,445 B2 | 7/2004 | Ramans et al. | |
| 6,773,327 B1 * | 8/2004 | Felice et al. | 446/330 |
| 6,817,972 B2 | 11/2004 | Snow | |
| 6,824,548 B2 | 11/2004 | Smith et al. | |
| 6,843,794 B2 | 1/2005 | Sixto, Jr. et al. | |
| 6,858,005 B2 | 2/2005 | Ohline et al. | |
| 6,902,560 B1 | 6/2005 | Morley et al. | |
| 6,942,613 B2 | 9/2005 | Ewers et al. | |
| 6,945,979 B2 | 9/2005 | Kortenbach et al. | |
| 6,960,162 B2 | 11/2005 | Saadat et al. | |
| 6,960,163 B2 | 11/2005 | Ewers et al. | |
| 6,976,969 B2 | 12/2005 | Messerly | |
| 6,994,700 B2 | 2/2006 | Elkins et al. | |
| 7,138,976 B1 | 11/2006 | Bouzit et al. | |
| 7,320,700 B2 * | 1/2008 | Cooper et al. | 606/205 |
| 7,480,600 B2 | 1/2009 | Massie et al. | |
| 7,553,275 B2 | 6/2009 | Padget et al. | |
| 2001/0023313 A1 | 9/2001 | Ide | |
| 2001/0042766 A1 * | 11/2001 | Ming-Shun | 224/324 |
| 2002/0096177 A1 | 7/2002 | Toti et al. | |
| 2002/0111604 A1 | 8/2002 | Doyle et al. | |
| 2002/0156497 A1 | 10/2002 | Nagase et al. | |
| 2002/0161281 A1 | 10/2002 | Jaffe et al. | |
| 2002/0177750 A1 | 11/2002 | Pilvisto | |
| 2003/0036748 A1 | 2/2003 | Cooper et al. | |
| 2003/0050649 A1 | 3/2003 | Brock et al. | |
| 2003/0078644 A1 | 4/2003 | Phan | |
| 2003/0109898 A1 | 6/2003 | Schwarz et al. | |
| 2003/0114838 A1 | 6/2003 | O'Neill et al. | |
| 2003/0135204 A1 | 7/2003 | Lee et al. | |
| 2003/0149338 A1 | 8/2003 | Francois et al. | |
| 2003/0153902 A1 | 8/2003 | Doyle et al. | |
| 2003/0229271 A1 | 12/2003 | Briscoe et al. | |
| 2003/0233026 A1 | 12/2003 | Saadat et al. | |
| 2004/0054322 A1 | 3/2004 | Vargas | |
| 2004/0138529 A1 | 7/2004 | Wiltshire et al. | |
| 2004/0138700 A1 | 7/2004 | Cooper et al. | |
| 2004/0236316 A1 | 11/2004 | Danitz et al. | |
| 2005/0090809 A1 | 4/2005 | Cooper et al. | |
| 2005/0096694 A1 | 5/2005 | Lee | |
| 2005/0107667 A1 | 5/2005 | Danitz et al. | |
| 2005/0119527 A1 | 6/2005 | Banik et al. | |
| 2005/0251112 A1 | 11/2005 | Danitz et al. | |
| 2005/0273084 A1 | 12/2005 | Hinman et al. | |
| 2005/0273085 A1 | 12/2005 | Hinman et al. | |
| 2006/0009759 A1 | 1/2006 | Chrisitian et al. | |
| 2006/0020287 A1 | 1/2006 | Lee et al. | |
| 2006/0036255 A1 | 2/2006 | Pond et al. | |
| 2006/0058582 A1 | 3/2006 | Maahs et al. | |
| 2006/0094931 A1 | 5/2006 | Danitz et al. | |
| 2006/0111209 A1 | 5/2006 | Hinman et al. | |
| 2006/0111210 A1 | 5/2006 | Hinman | |
| 2006/0111615 A1 | 5/2006 | Danitz et al. | |
| 2006/0199999 A1 | 9/2006 | Ideda et al. | |
| 2010/0041945 A1 | 2/2010 | Isbell, Jr. | |

FOREIGN PATENT DOCUMENTS

| | | |
|---|---|---|
| EP | 0 598 618 A2 | 5/1994 |
| EP | 0 836 833 A2 | 4/1998 |
| EP | 0 836 833 A3 | 4/1998 |
| EP | 1 132 041 A2 | 9/2001 |
| EP | 1 395 398 B1 | 3/2004 |
| JP | H06-262549 | 9/1994 |
| JP | 01-299768 | 10/2001 |
| WO | WO98/49961 A1 | 11/1998 |
| WO | WO 01/10292 A1 | 2/2001 |
| WO | WO-02/13682 A1 | 2/2002 |
| WO | WO-2004/019769 A1 | 3/2004 |
| WO | WO-2004/105578 A2 | 12/2004 |
| WO | WO-2004/105578 A3 | 12/2004 |
| WO | WO-2004/105578 C2 | 12/2004 |
| WO | WO 2005/067785 A1 | 7/2005 |
| WO | WO-2005/120326 A2 | 12/2005 |
| WO | WO-2005/120326 A3 | 12/2005 |
| WO | WO-2005/120327 A2 | 12/2005 |
| WO | WO-2005/120327 A3 | 12/2005 |
| WO | WO-2006/057699 A1 | 6/2006 |
| WO | WO-2006/057700 A1 | 6/2006 |
| WO | WO-2006/057702 A2 | 6/2006 |
| WO | WO 2006/073581 A1 | 7/2006 |

OTHER PUBLICATIONS

Hegeman et al; U.S. Appl. No. 11/787,543 entitled "Tool with articulation lock," filed Apr. 16, 2007.

Hinman, Cameron; U.S. Appl. No. 11/787,607 entitled "Tool with rotation lock," filed Apr. 16, 2007.

Hinman, Cameron; U.S. Appl. No. 11/787,605 entitled "Tool with multi-state ratcheted end effector," filed Apr. 16, 2007.

Hinman et al; U.S. Appl. No. 11/787,599 entitled "Tool with end effector force limiter," filed Apr. 16, 2007.

Hegeman et al; U.S. Appl. No. 11/787,201 entitled "Articulating tool with improved tension member system" filed Apr. 16, 2007.

Danitz et al.; U.S. Appl. No. 12/109,333 entitled "Articulating instrument," filed Apr. 24, 2008.

U.S. Appl. No. 10/928,479, filed Aug. 26, 2004 for Hinman et al., 57 pages.

U.S. Appl. No. 10/948,911, filed Sep. 24, 2004 for Danitz et al., 52 pages.

U.S. Appl. No. 10/997,372, filed Nov. 23, 2004 for Danitz et al., 78 pages.

International Search Report mailed on Jan. 25, 2006 for PCT Application No. PCT/US2005/033257 filed on Sep. 15, 2005, 4 pages.

U.S. Appl. No. 11/344,465, filed Jan. 30, 2006 for Danitz, 28 pages.

Cox, James; The minimally invasive Maze-III procedure; Operative Techniques in Thoracic and Cardiovascular Surgery; vol. 5; No. 1; pp. 79-92; Feb. 2000.

Simha et al.; The elctrocautery maze—how I do it; The Heart Surgery Forum; vol. 4; No. 4; pp. 340-345; Aug. 23, 2001.

Prasad et al.; Epicardial ablation on the beating heart: progress towards an off-pump maze procedure; The Heart Surgery Forum; vol. 5/ No. 2; pp. 100-104; Jun. 27, 2001.

Hinman, Cameron; U.S. Appl. No. 12/508,478 entitled "Articulating mechanism," filed Jul. 23, 2009.

Hinman et al.; U.S. Appl. No. 12/725,377 entitled "Articulating mechanism with flex-hinged links," filed Mar. 16, 2010.

Danitz et al.; U.S. Appl. No. 12/766,818 entitled "Articulating instruments with joystick control," filed Apr. 23, 2010.

Danitz, David J.; U.S. Appl. No. 12/766,820 entitled "Articulating mechanism with bifurcating control," filed Apr. 23, 2010.

Danitz, David J.; U.S. Appl. No. 12/766,822 entitled "Articulating catheters," filed Apr. 23, 2010.

Danitz, David J.; U.S. Appl. No. 12/766,825 entitled "Articulating endoscopes," filed Apr. 23, 2010.

Danitz, David J.; U.S. Appl. No. 12/766,827 entitled "Articulating retractors," filed Apr. 23, 2010.

Hinman et al.; U.S. Appl. No. 12/816,359 entitled "Link systems and articulation mechanisms for remote manipulation of surgical or diagnostic tools," filed Jun. 15, 2010.

* cited by examiner

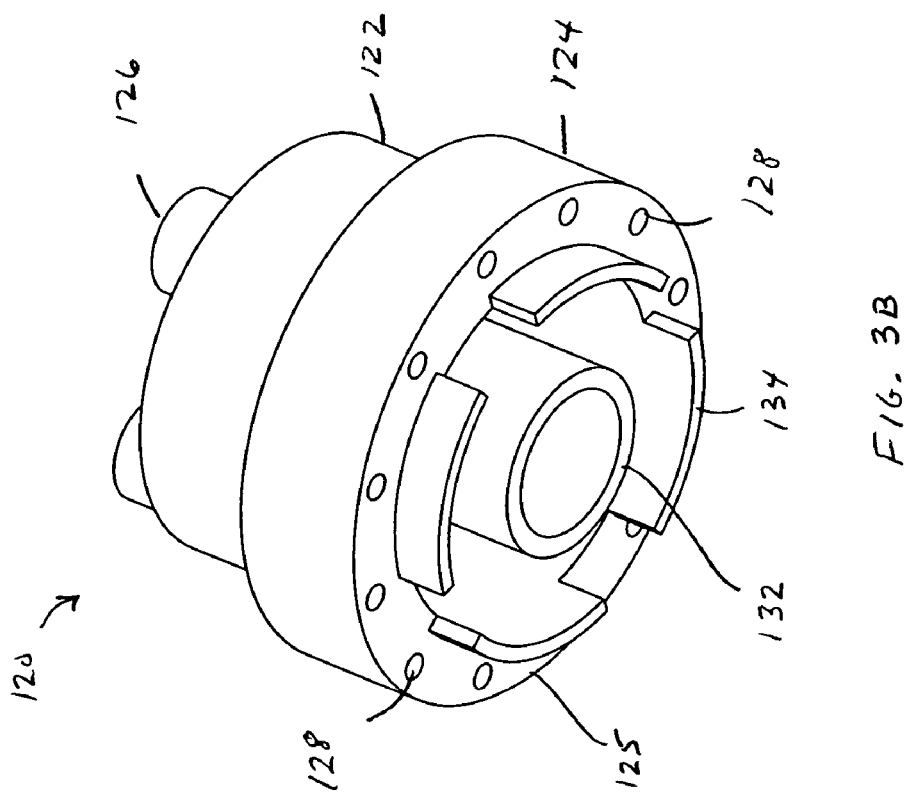
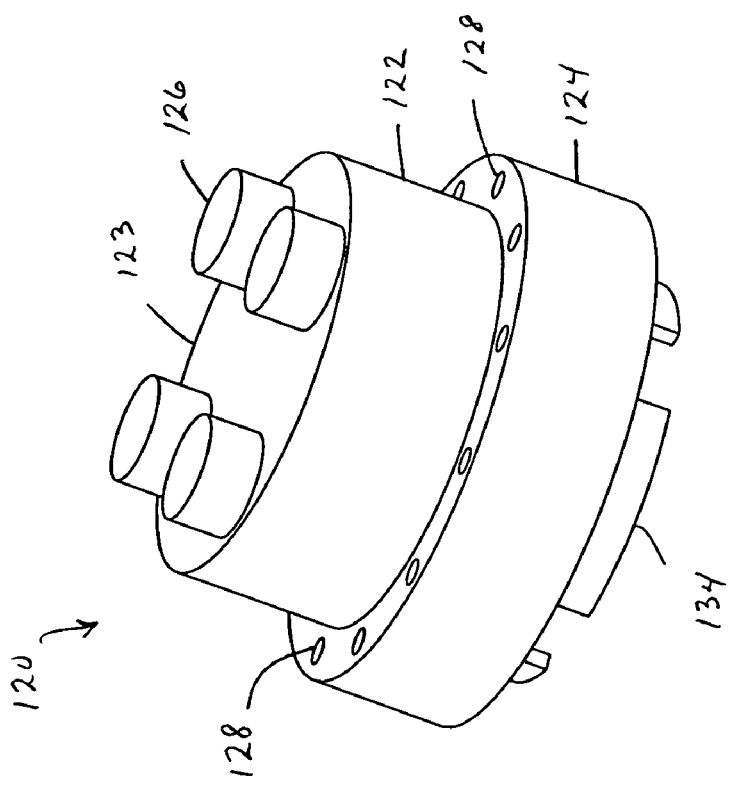
FIG. 3B
FIG. 3A

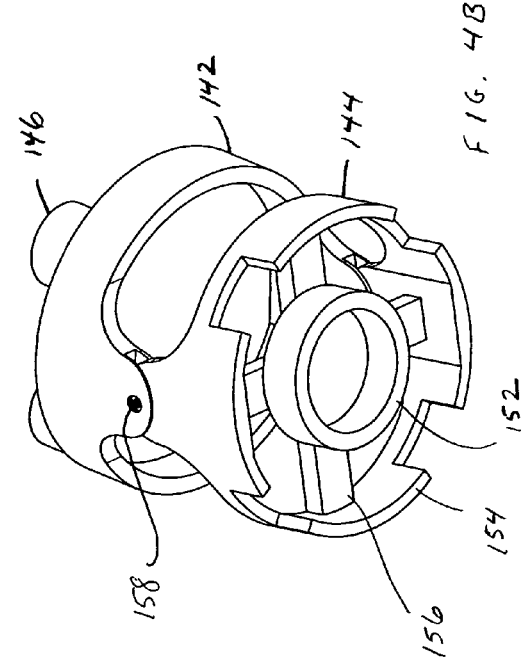
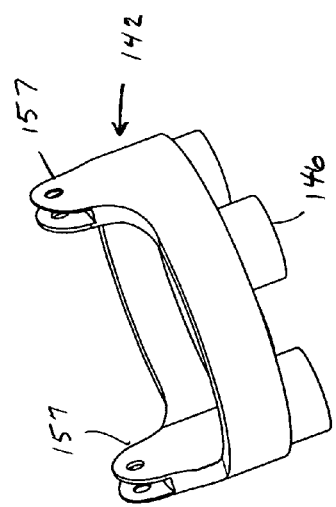
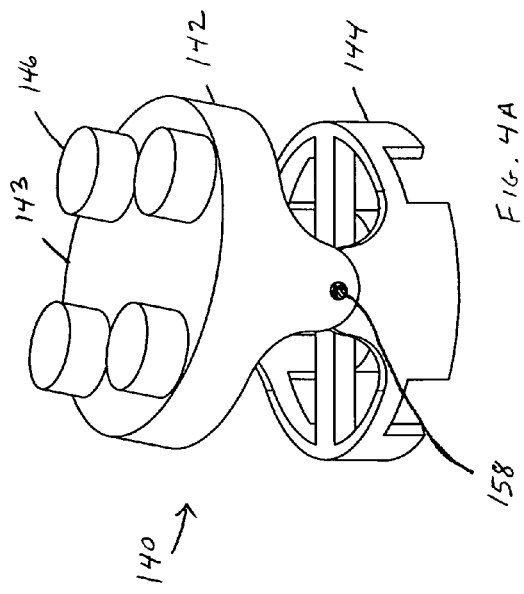
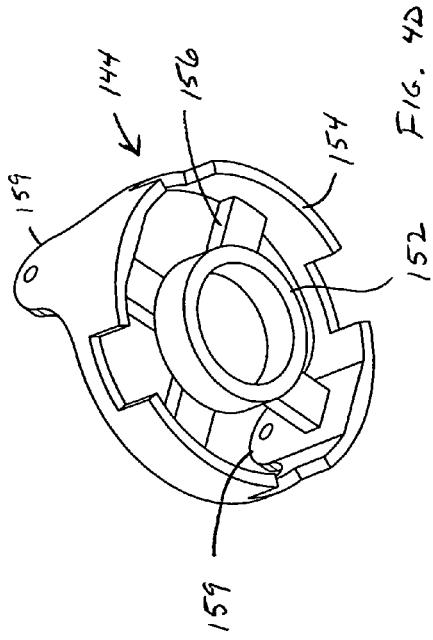

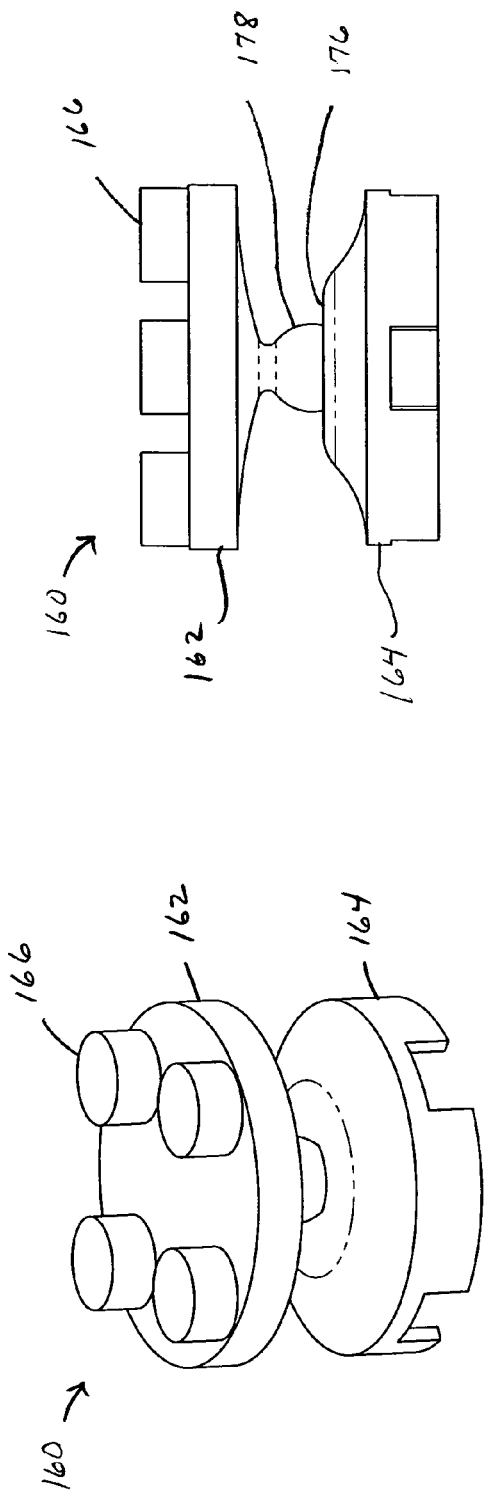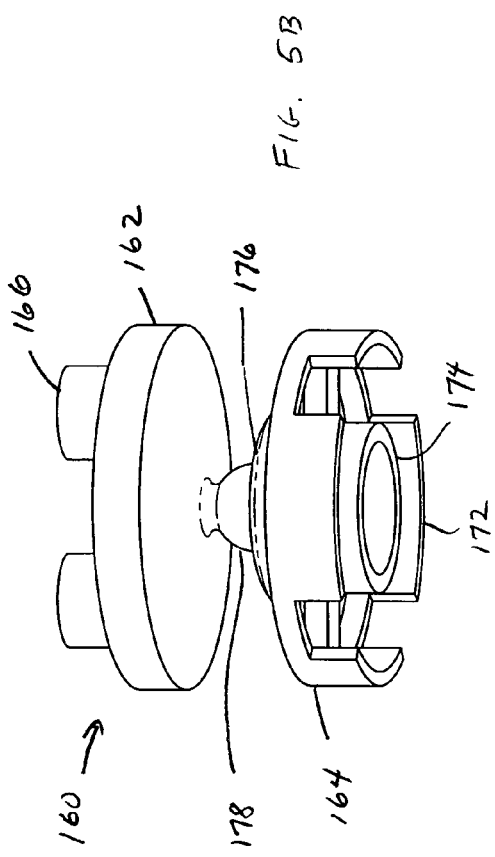

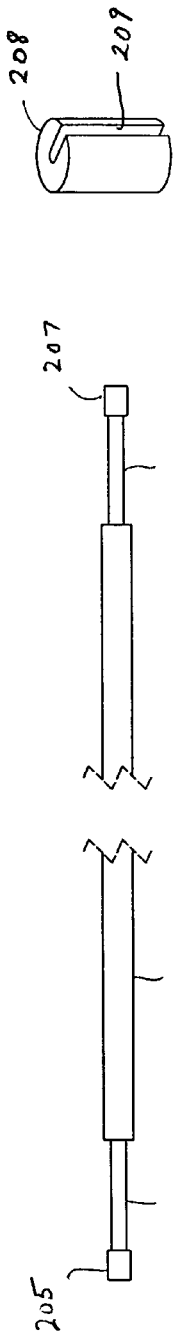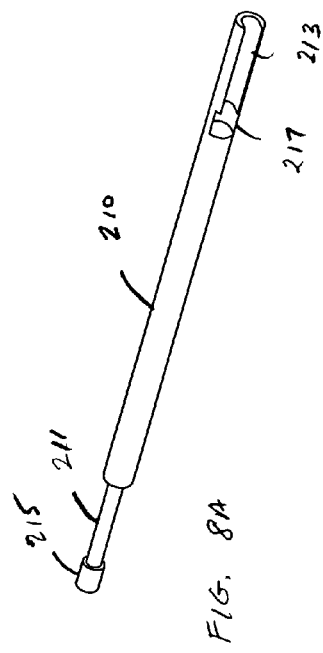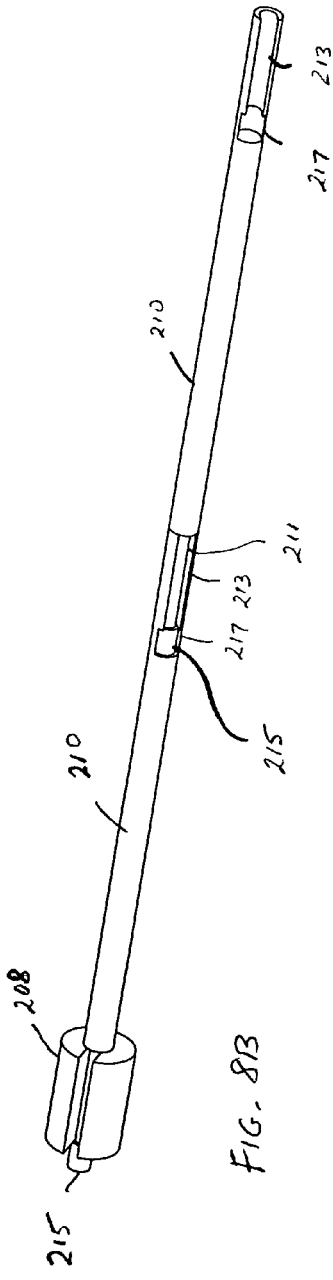

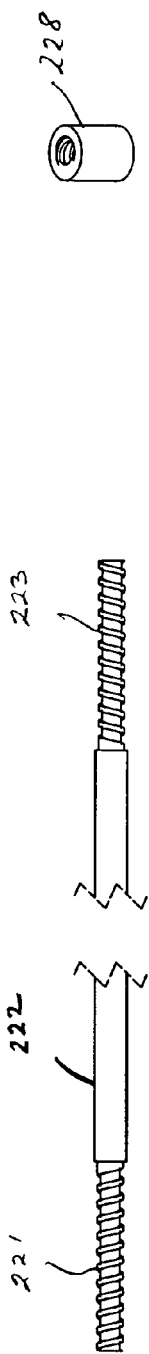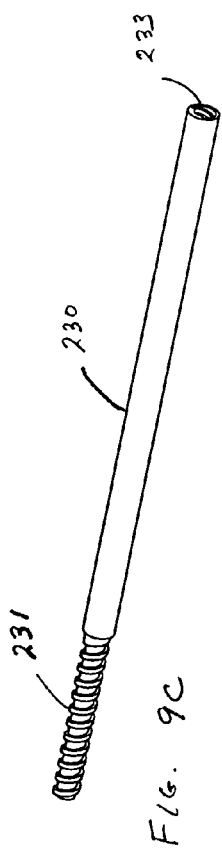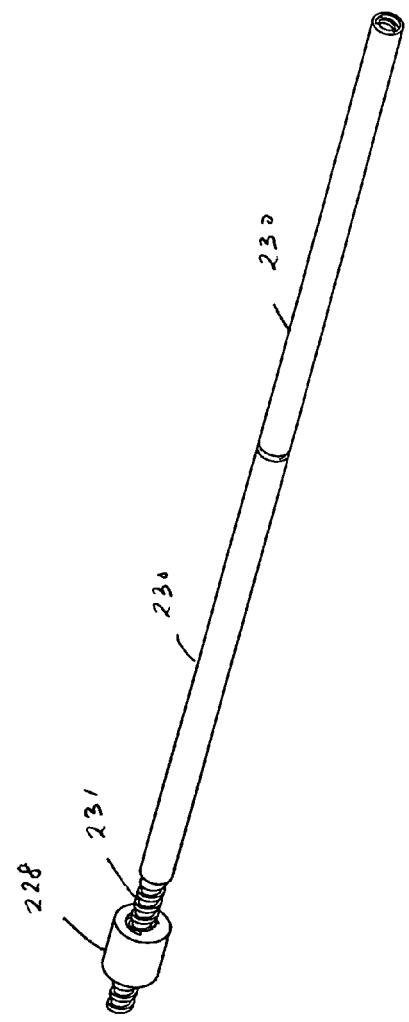

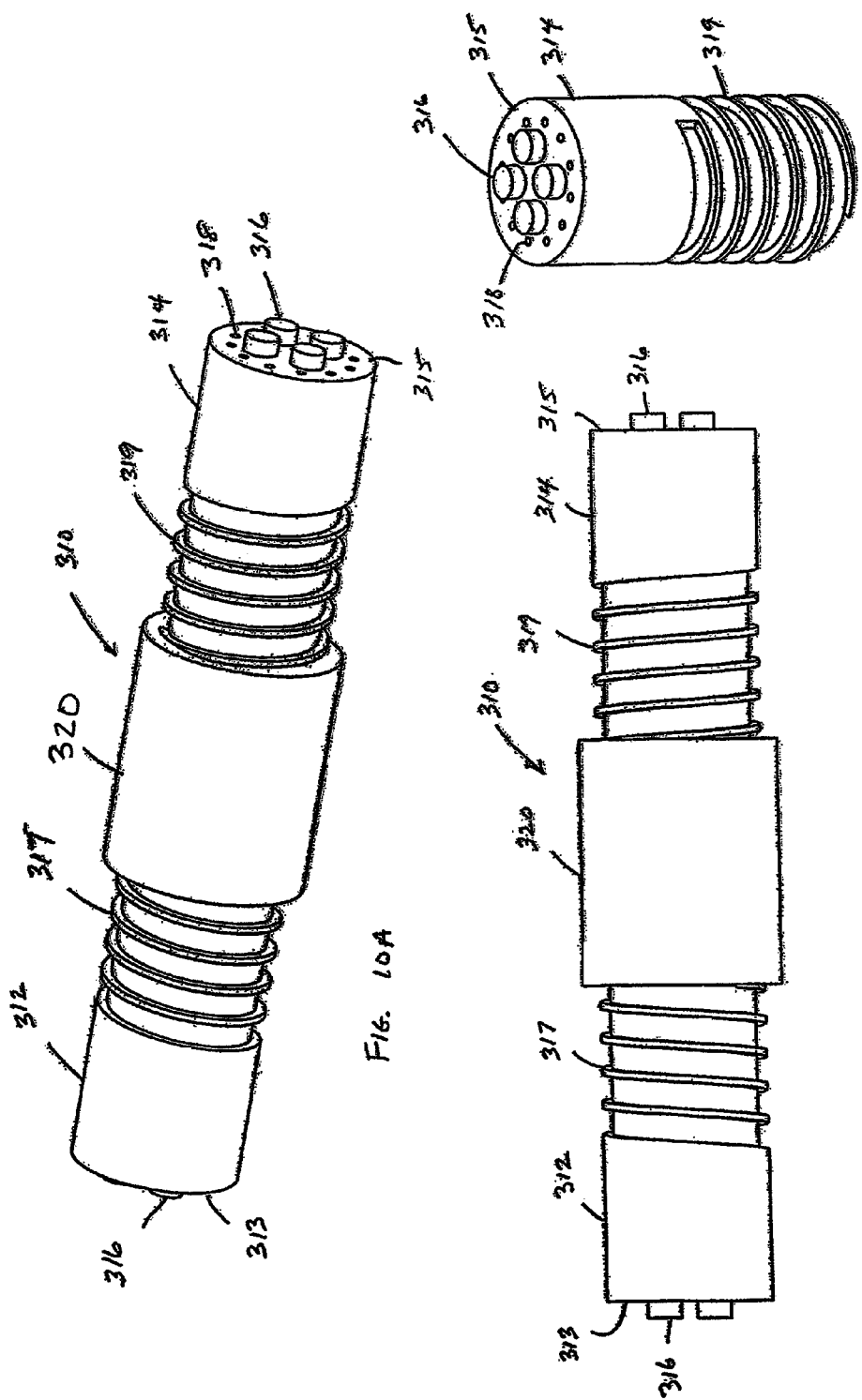

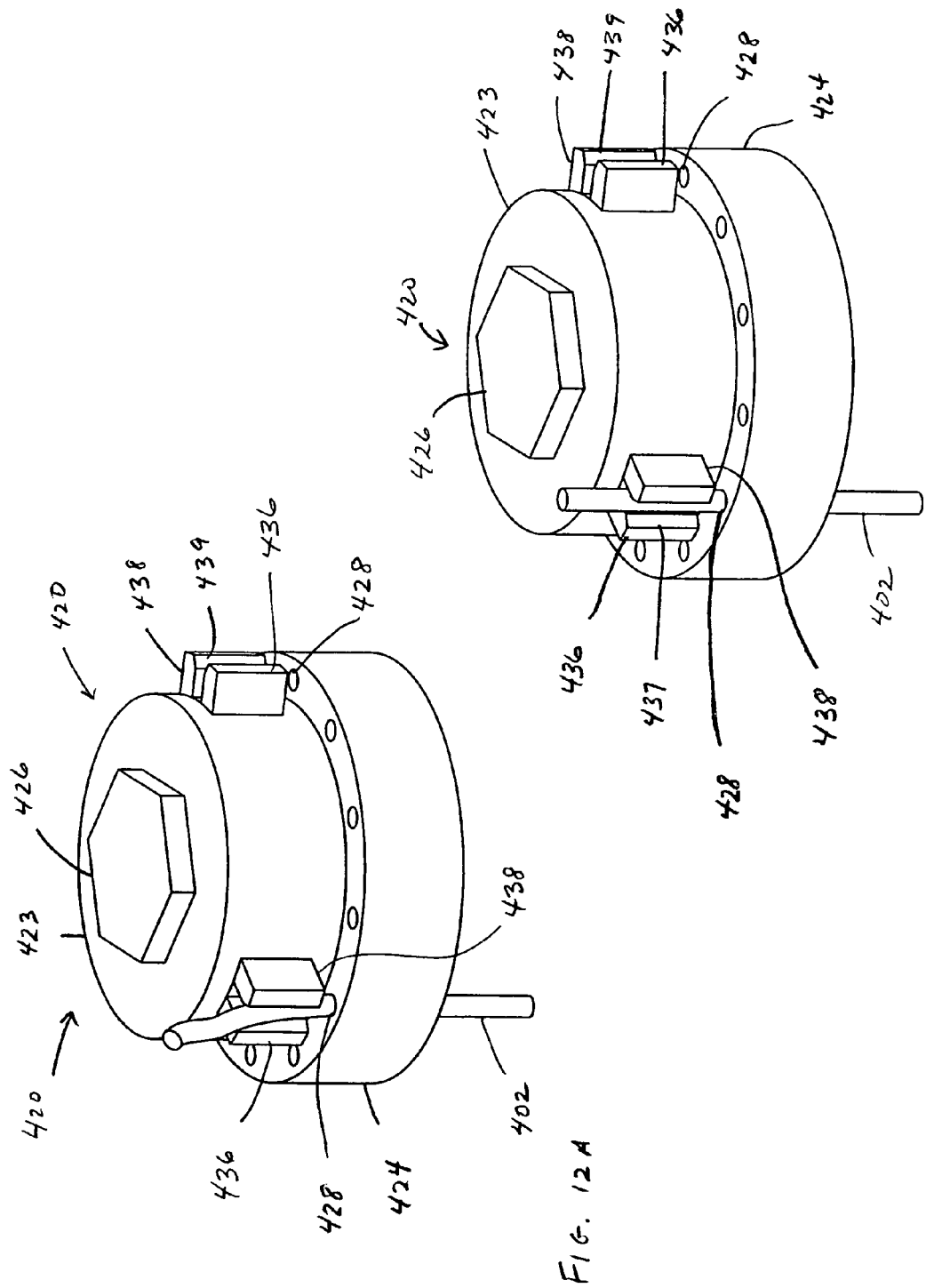

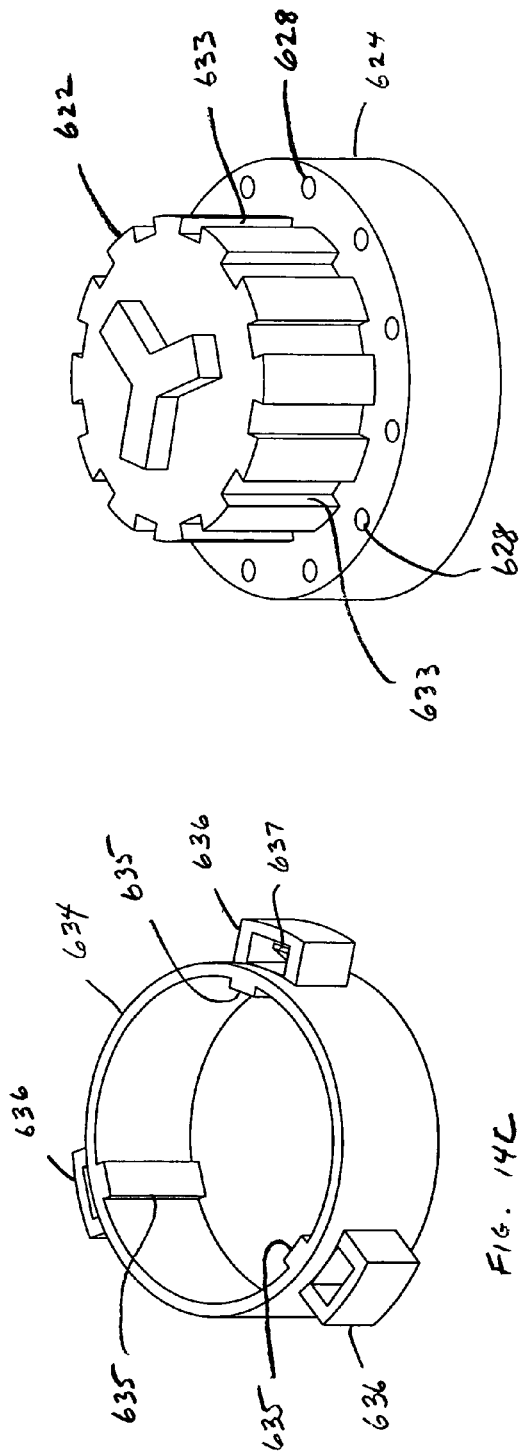
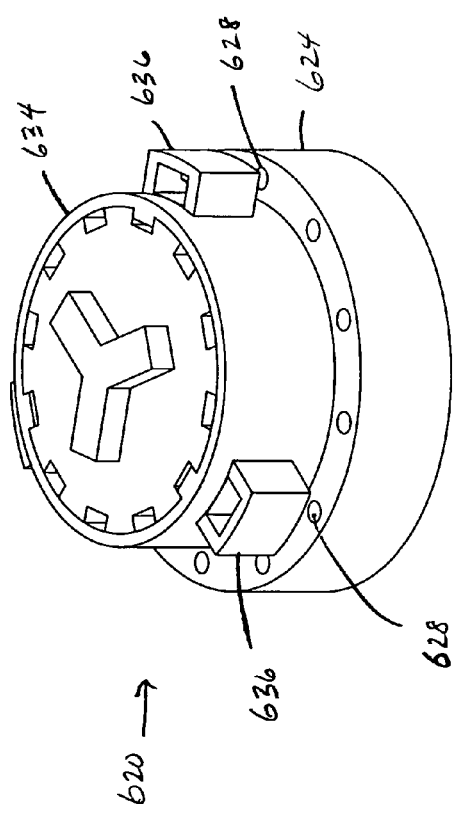
FIG. 14B
FIG. 14A
FIG. 14C

ARTICULATING MECHANISM COMPONENTS AND SYSTEM FOR EASY ASSEMBLY AND DISASSEMBLY

CROSS-REFERENCE TO RELATED APPLICATIONS

This application claims the benefit of U.S. Provisional Application No. 60/630,912, filed Nov. 24, 2004, the contents of which is hereby incorporated by reference into the present disclosure.

BACKGROUND OF THE INVENTION

This invention relates to articulating mechanisms and devices that can be easily assembled and disassembled, and to systems and components to assemble such articulating mechanisms and devices.

The ability to easily remotely steer, guide and/or manipulate instruments and tools is of interest in a wide variety of industries and applications, in particular where it is desired to navigate an instrument or tool into a workspace that is not easy to manually navigate by hand or that might otherwise present a risk or danger. These can include situations where the targeted site for the application of a tool or instrument is difficult to access, e.g. certain surgical procedures, or the manufacture or repair of machinery, or even commercial and household uses, where manual access to a targeted site is restricted or otherwise. Other situations can include e.g. industrial applications where the work environment is dangerous to the user, for example, workspaces exposed to dangerous chemicals. Still other situations can include e.g. law enforcement or military applications where the user may be at risk, such as deployment of a tool or instrument into a dangerous or hostile location. Other uses include recreational, educational, or entertainment applications, such as toys that provide for remote manipulation of an object.

Using surgical procedures as an illustrative example, procedures such as endoscopy and laparoscopy typically employ instruments that are steered within or towards a target organ or tissue from a position outside the body. Examples of endoscopic procedures include sigmoidoscopy, colonoscopy, esophagogastroduodenoscopy, and bronchoscopy. Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues. Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures. Steerable catheters are also well known for both diagnostic and therapeutic applications. Similar to endoscopes, such catheters include tips that can be directed in generally limited ranges of motion to navigate a patient's vasculature.

There have been many attempts to design endoscopes and catheters with improved steerability. For example, U.S. Pat. No. 3,557,780 to Sato; U.S. Pat. No. 5,271,381 to Ailinger et al.; U.S. Pat. No. 5,916,146 to Alotta et al.; and U.S. Pat. No. 6,270,453 to Sakai describe endoscopic instruments with one or more flexible portions that may be bent by actuation of a single set of wires. The wires are actuated from the proximal end of the instrument by rotating pinions (Sato), manipulating knobs (Ailinger et al.), a steerable arm (Alotta et al.), or by a pulley mechanism (Sato). U.S. Pat. No. 5,916,147 to Boury et al. discloses a steerable catheter having four wires that run within the catheter wall. Each wire terminates at a different part of the catheter. The proximal ends of the wires extend loosely from the catheter so that the physician may pull them. The physician is able to shape and thereby steer the catheter by selectively placing the wires under tension.

Although each of the devices described above are remotely steerable, their range of motion is generally limited. The steering mechanisms may also be laborious to use, such as in the catheter of Boury et al. where each wire must be separately pulled to shape the catheter. Further, in the case of e.g. endoscopes and steerable catheters that use knob and pulley mechanisms, it requires a significant amount of training to become proficient in maneuvering the device through a patient's anatomy.

Consequently, a device with enhanced remote maneuverability to controllably navigate complex geometries may allow more efficient and precise advancement and deployment of instruments and tools. It would also be advantageous for such a device to provide a more intuitive and facile user interface to achieve such enhanced maneuverability. Such a device would have widespread application in guiding, steering and/or manipulating instruments and tools across numerous industries. Such a device would also of itself have entertainment, recreation and educational value. In addition it would also be advantageous for such devices to be formed of components that can be manually assembled, such that a user can readily form devices of varying dimensions and characteristics, as desired.

BRIEF SUMMARY OF THE INVENTION

The present invention meets these and other needs and provides for systems and components for quickly and easily assembling and/or disassembling an articulating mechanism. In one variation of the invention, a system is provided having two or more link components and two or more joint components, and one or more sets of connecting cables that can be releasably secured against the link components. The connecting cables operably connect one link component with another link component to form a link component pair. In certain variations, the link and joint components can be adapted to releasably connect to one another. The joint components are designed for pivoting or flexing movement. The link components include channels for the receipt and passage of the connecting cables. The system can optionally include spacer and/or central components. The spacer and/or central components can likewise be adapted to releasably connect to the link and joint components and can further include channels for receipt and passage of connecting cables. The releasable connection between components can, but need not be, an interference-fit or snap-fit connection. Advantages of using releasable connections includes ease of assembly and an increased ability to transmit torque along an assembled mechanism.

In another variation of the invention, an articulating mechanism is provided that is assembled from such components. In further variations, the system or assembled mechanism can include the provision of cable extenders that allow the formation of customized lengths of connecting cables. Additionally, various means are provided to secure the connecting cables to the associated link component pair. In certain variations, these include cable stops that attach to the cables themselves. In other variations, cable anchors are provided on the link components themselves. Additionally, in certain variations the cables can be tensioned, either individually or collectively. Any or all of the components can be further provided with channels that allow for the passage of wires, other cables, fiber optics, and other elements that may be connected to or involved in controlling a tool, instrument, or other element deployed at an end or any section of the assembled mechanism.

BRIEF DESCRIPTION OF THE DRAWINGS

FIGS. 3A-3B are enlarged perspective views of a link component of the assembled articulating mechanism of FIG. 1;

FIGS. 4A-4B are enlarged perspective views of a joint component of the assembled articulating mechanism of FIG. 1; FIGS. 4C and 4D are perspective views of individual parts of the joint component of FIGS. 4A-4B;

FIGS. 5A-5B are enlarged perspective views of another joint component of the assembled articulating mechanism of FIG. 1; FIG. 5C is a side view of the joint component of FIGS. 5A-5B;

FIG. 7A is an enlarged side view of one of the connecting cables of the articulating mechanism of FIG. 1; FIG. 7B is a perspective view of a cable stop for use with the connecting cable of FIG. 7A;

FIG. 8A is a perspective view of a cable extender for use with the connecting cable of FIG. 7A; FIG. 8B is a perspective view of cable extenders of FIG. 8A joined together;

FIG. 9A is an enlarged side view of a connecting cable according to another embodiment of the invention; FIG. 9B is a perspective view of a cable stop for use with the connecting cable of FIG. 9A; FIG. 9C is a perspective view of a cable extender for use with the connecting cable of FIG. 9A; FIG. 9D is a perspective view of cable extenders of FIG. 9C joined together;

FIGS. 10A and 10B are perspective and side views, respectively, of a central component according to another embodiment of the invention; FIG. 10C is a perspective view of a section of the central component of FIG. 10A;

FIGS. 12A-12B are perspective views of the link component of FIGS. 11A-11B, showing attachment of a connecting cable to the link component;

FIG. 14A is a perspective view of a link component according to a further embodiment of the invention; and FIGS. 14B and 14C are perspective views of parts of the link component of FIG. 14A.

DETAILED DESCRIPTION OF THE INVENTION

Figure 1A:
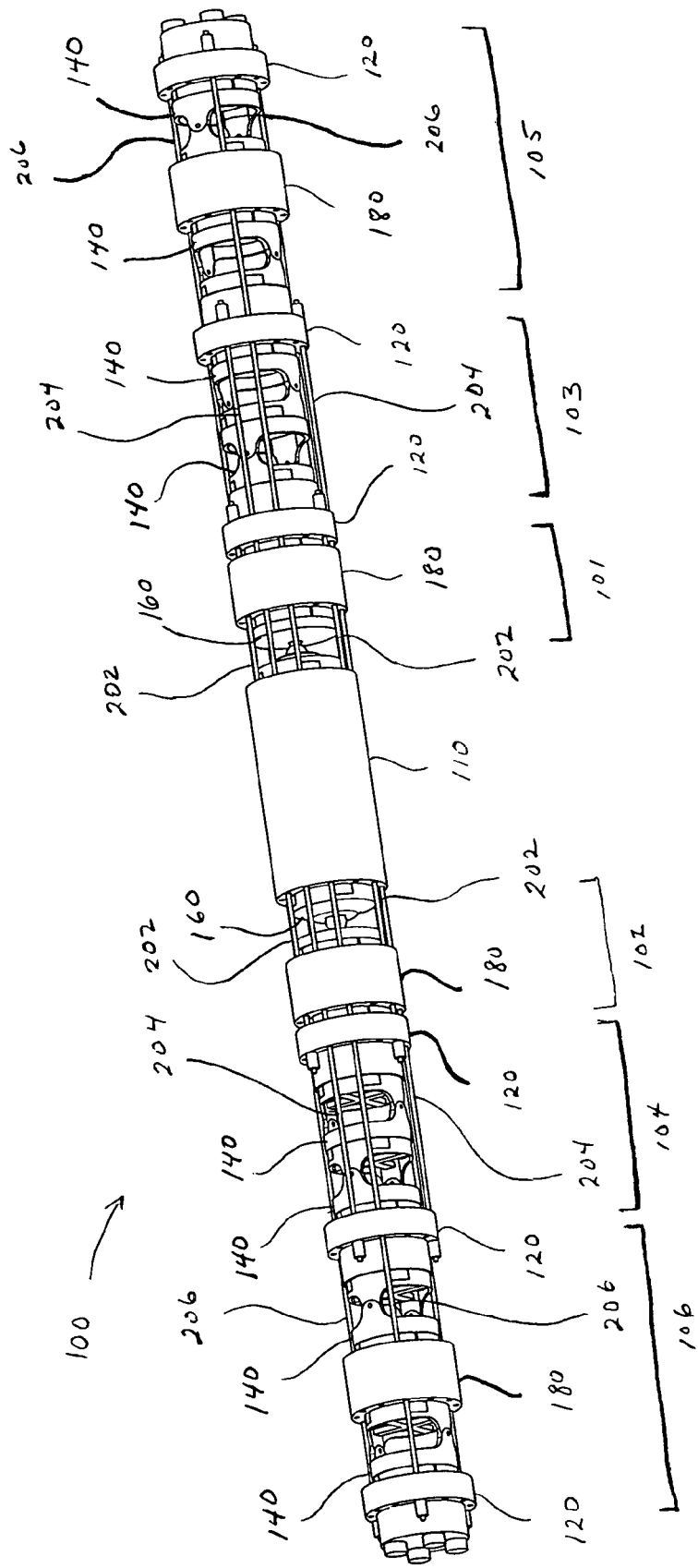
FIG. 1A is a perspective view of an articulating mechanism according to one embodiment of the invention, as assembled from a central component, joint, link and spacer components, and connecting cables.

The component-based system for assembling articulating mechanisms according to the invention generally includes a variety of link, joint, central and spacer components together with connecting cables of varying lengths. The link and joint components can be connected together, to form individual link-joint units, which in turn can be connected to other link-joints units, additional joint components, spacer components or a central component. A wide variety of designs are available for forming releasable connections between the various components, as will be apparent to one of skill in the art, including reciprocal interference-fit and snap-fit connections. Link-joint units that are separated by the central component can then be connected together by at least one set of cables to form discrete pairs. Alternatively, the various components can be designed to abut one another in a reciprocal fashion, in which case the cable sets themselves will hold the assembled mechanism together. By mixing and matching link, joint, central, spacer components, articulating mechanisms with varying lengths, bending, and rigidity characteristics can be formed. The components or formed articulating mechanisms can be incorporated into or integrally formed with other structures, or elements of other structures, including tools, instruments, or in the case of e.g. recreational uses, toys, puppets, dolls, figurines, and the like.

The term "link component" as used herein refers to a discrete component of an articulating mechanism. Link components can be optionally designed to releasably interconnect to other components of an assembled articulating mechanism, including joint components, spacer components and central components. When assembled, link components are generally aligned along the longitudinal axis of the assembled mechanism. Link components are typically, but need not be, cylindrical. Link components will usually further include multiple cables channels spaced radially from the longitudinal axis of the link component. These cable channels are configured for receipt and passage of cables, including cables that control the movement of the particular link component as well as cables that pass through the link component and control other link components. A given cable channel can be designed to accommodate a single cable or multiple cables, and can be positioned at varying radially spaced locations. Link components can be further provided with additional channels that allow for the passage of wires, other cables, fiber optics, and other elements that may be connected to or involved in controlling a tool, instrument, or other element deployed at an end or any section of the assembled mechanism.

The term "joint component" as used herein refers to another discrete component of an articulating mechanism. Joint components can similarly be optionally designed to releasably interconnect to other components of an assembled articulating mechanism, including link components, other joint components, spacer components and central components. Joint components are also typically, but need not be, cylindrical. Joint components typically include two sections that are moveable relative to each other. As examples, the two sections can be pivotally coupled to each other for pivoting motion, or the two sections can be connected by a flexure for flexing or bending motion between the two sections. Like link components, joint components can also further include multiple cables channels spaced radially from the longitudinal axis of the joint component. These cable channels are configured for receipt and passage of cables, including cables that control the movement of link components. Joint components can also be further provided with channels that allow for the passage of wires, other cables, fiber optics, and other elements that may be connected to or involved in controlling a tool, instrument, or other element deployed at an end or any section of the assembled mechanism.

The term "link-joint unit" as used herein refers to a link component connected (directly or indirectly) to a joint component. In certain variations, the link component and joint component can be integrally formed as a single piece, such as shown in FIGS. 6C and 6D, for example. In other variations, link-joint units can include intervening spacer components between the link and the joint component. The term "active link-joint units" refers to a pair of link-joint units where the corresponding link components of each unit are directly connected to one another by a cable set.

The term "spacer component" as used herein refers to yet another discrete component of an articulating mechanism. Again, spacer components can be optionally designed to releasably interconnect to other components of an assembled articulating mechanism, including link components, other joint components, spacer components and central components. They are also typically, but need not be, cylindrical. Similar to link components, spacer components will typically, but need not always, include multiple cables channels spaced radially from the longitudinal axis of the link. These cable channels are configured for receipt and passage of cables that control link components located elsewhere on the assembled mechanism. Likewise, spacer components can also be further provided with channels that allow for the passage of wires, other cables, fiber optics, and other elements that may be connected to or involved in controlling a tool, instrument, or other element deployed at an end or any section of the assembled mechanism. In certain variations, spacer and joint components can be combined to form spacer-joint units in a similar manner as for link-joint units.

The term "central component" as used herein refers to a further optional component of an articulating mechanism. Like the other components, central components are also optionally designed to releasably interconnect to other components of an assembled articulating mechanism, including link components, joint components, and spacer components. When assembled, the central component may define the longitudinal axis of the assembled mechanism in its unarticulated state. The central component can function to separate the link component pairs of link-joint unit pairs, and in a more general sense separate or space apart the proximal and distal ends of an assembled mechanism. Central components can be provided in varying lengths, such that the distance between the proximal and distal ends of the assembled mechanism can be altered, as desired. Central components can also be provided having varying rigidities, for example the central component can be relatively stiff, or it can have some flexibility, such as when incorporated e.g. into the flexible shaft of an endoscope. Central components are typically but need not be cylindrical. Central components further provide for passage of control cables. Typically, central components, like the other components, will include multiple cables channels spaced radially from the longitudinal axis of the component that receive such cables. As with other components, central components can be incorporated into or integrally formed with other structures, or elements of other structures. For example, in the case of toys, the central component can be integrally formed with the body of the toy, with other combinations of components forming e.g. various appendages, such as the head and tail of the toy.

The term "cable set" as used herein refers to a set or arrangement one or more cables that operably connect a pair of links or link-joint units to one another.

The terms "instrument" and "tool" are herein used interchangeably and refer to devices that are usually handled by a user to accomplish a specific purpose. In further aspects of the invention, a tool or instrument may be attached to and extend from one end of the assembled articulating mechanisms for use in a wide variety of applications. Generally, any such application will include situations where it is desirable to navigate an instrument or tool into a workspace that is not easy to manually navigate by hand or that might otherwise present a risk or danger. In the case of surgical applications, examples of surgical or diagnostic tools include, but are not limited to, endoscopes, light sources, catheters, Doppler flow meters, microphones, probes, retractors, dissectors, staplers, clamps, graspers, scissors or cutters, and ablation or cauterizing elements. For other applications, numerous tools or instruments are likewise contemplated, including without limitation, e.g., graspers, drivers, power tools, welders, magnets, optical lenses and viewers, electrical tools, audio/visual tools, lasers, light sources, monitors, and the like. Such other applications include, without limitation, industrial uses, such as for the navigation of a tool, probe, sensor, etc. into a constricted space, or for precise manipulation of a tool remotely, for example, for the assembly or repair of machinery. These can also include commercial and household situations where the targeted site for the application of a tool or instrument is difficult to access. Other situations can include e.g. industrial applications where the work environment is dangerous to the user, for example, workspaces exposed to dangerous chemicals. Still other situations can include e.g. law enforcement or military applications where the user may be at risk, such as deployment of a tool or instrument into a dangerous or hostile location. Yet other uses include applications where simply remote manipulation of complex geometries is desirable. These include uses in recreation, education, or entertainment, such as toys or games, e.g., for remote manipulations of or integration into puppets, dolls, figurines, and the like. The types of tools or instruments, methods and locations of attachment to assembled articulating mechanisms, and applications and uses include, but are not limited to, those described in pending and commonly owned U.S. application Ser. Nos. 10/444,769, 10/928,479, 10/948,911, and 10/997,372 incorporated herein by reference in their entireties.

Figure 1B:
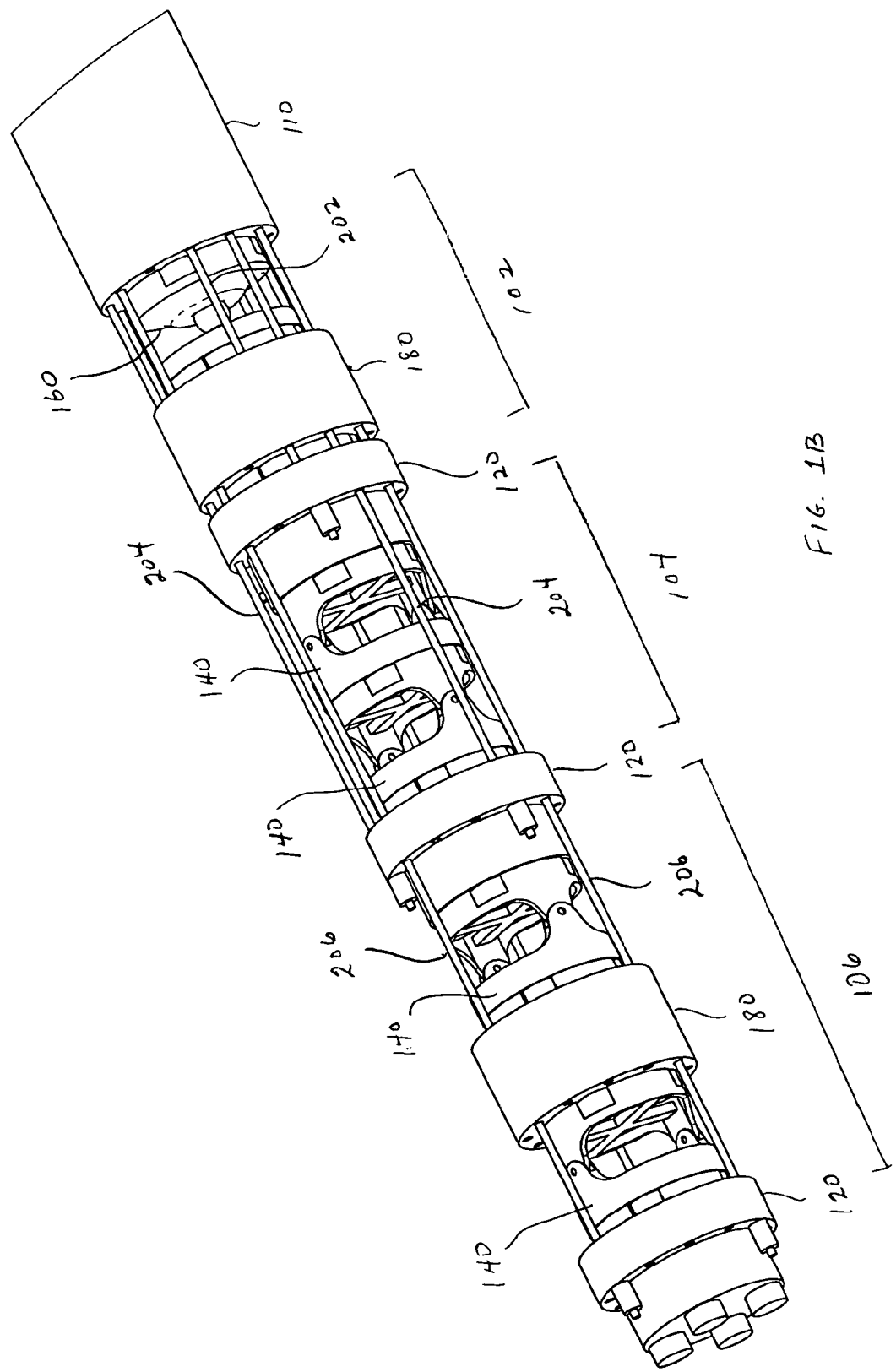
FIG. 1B is a enlarged perspective view of the assembled articulating mechanism of FIG. 1A.
Figure 2:
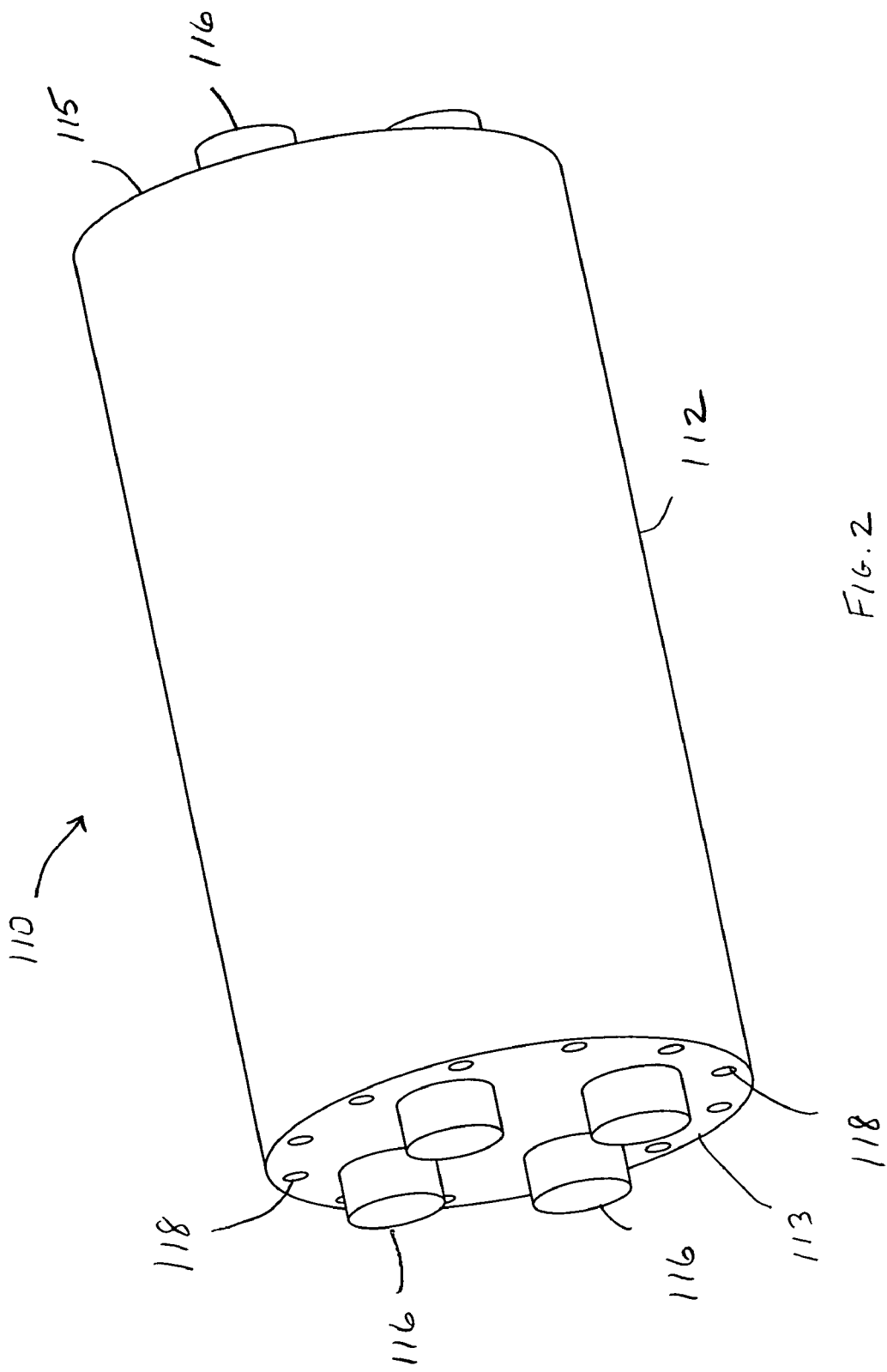
FIG. 2 is an enlarged perspective view of the central component of the assembled articulating mechanism of FIG. 1.

Turning to FIGS. 1A-1B, articulating mechanism 100 is assembled from a number of separate components, including central component 110, link components 120, joint components 140 and 160, and spacer components 180. Link, joint and spacer components are positioned on either side of the central component, to create first (or proximal) and second (or distal) sections separated by the central component. Pairs of link components are connected by sets of cables 202, 204 and 206, with the members of each pair positioned on opposite sides of central component 100, such that movement of one link component of the pair causes a corresponding movement of the other link component of the pair. Such movement is possible due to the joint components which are capable of pivoting movement. Each link component is connected (either directly or indirectly) to at least one joint component to form a link-joint unit. The sets of cables 202, 204 and 206 are releasably secured to the link-joint units by an adjoining component 208, of FIG. 8B. The adjoining component 208 can provide a snap-fit connection to the sets of cables 202, 204, and 206, while abutting at least one of the link-joint units due to the tension in the sets of cables 202, 204, and 206. The ability to manipulate link component pairs allows for the mechanism to readily form complex three-dimensional configurations and geometries as is further detailed herein and as generally described in pending U.S. application Ser. No. 10/444,769, incorporated herein in its entirety:

As seen more clearly in FIG. 2, central component 110 is generally cylindrical with opposite ends 113 and 115, each with multiple tubular projections 116 extending from the ends. These projections are configured to achieve a snap-fit connection with other components, i.e., link, joint or spacer components as further described. Cable channels 118 are positioned at a radial distance from the central axis of the component and extend through the component, and opening at each end 113 and 115. These cable channels allow for passage of the cable sets that connect link components on the proximal and distal sections of the assembled mechanism. As depicted, channels 118 are fully enclosed, but one of skill in the art will appreciate that other channels designs will also function effectively. In this design, proximal and distal ends of the assembled mechanism will exhibit inverted motion relative to one another. Alternatively, the central component can be hollow, with the cables received through inlet ports at either end and routed through the hollow interior of the central component. This would allow for twisting of the cables as they are passed through central component, producing other relative reciprocal movements of the proximal and distal ends of the assembled mechanism. For example, a 180 degree twist will produce mirrored movement. Central components of varying lengths can be provided, depending on the desired distance between the proximal and distal sections of the assembled mechanism. Alternatively, the central component can include cable channels with a predetermined twist to achieve the desired reciprocal motion. The central component in general provides flexibility to the system. By providing central components of differing lengths, the resultant assembled mechanisms can have their corresponding joint, link and/or spacer component pairs spaced farther apart or closer together. Central components also provide for easier assembly of resultant mechanisms in situations where the central component and the joint, link and/or spacer component are releasably connectable to one another, as the central component can be the starting point for attachment of subsequent components. However, it will also be appreciated that articulating mechanisms can be assembled without a central component, as long as at least two link-joint components are assembled that are oriented opposite to one another.

FIGS. 3A-3B show link component 120 in greater detail. Body 122 of link component 120 is generally cylindrical and includes rim section 124 that extends radially outward from body 122. Rim section 124 includes cable channels 128 that extend through the rim section for receiving cable sets. As depicted, channels 128 are also fully enclosed. Again, one of skill in the art will appreciate that other channels designs will also function effectively provided the routed cables are maintained within the channel. Also, while cable channels 128 as depicted are located in rim section 124, it will be appreciated that cable channels can be located at any radial location from the link component longitudinal axis, and that such rim sections are not necessary. Tubular projections 126 extend from end 123 of the link component, similar to projections 116 of central component 110. Opposite end 125 includes integral hollow tubes 132 and 134, with interior tube 132 nested within exterior tube 134. The tubular projections 126 and the tubes 132 and 134 oriented and configured such that the tubular projections of one link component can be received within the space between tubes 132 and 134 and thereby engage with tubes 132 and 134 in snap-fit arrangement. This interlocking tube system is similar to that used, for example, in interlocking plastic blocks, such as those sold under the brand name LEGO® (Billund, Denmark). Similarly dimensioned tubular projections and hollow tubes are likewise provided on joint and spacer components 140, 160 and 180 such that any such components can be connected to a link component 120 or to each other. Central component 110 also has similarly dimensioned tubular projections and can likewise connect to a link, joint or spacer component 120, 140, 160 and 180 in like fashion.

FIGS. 4A-4D show joint component 140 in greater detail. Joint component 140 is formed of two sections 142 (FIG. 4C) and 144 (FIG. 4D) that are hinged together. As depicted, hinge pins 158 connect brackets 157 that extend from section 142 to arms 159 extending from section 144, such that the sections can pivot relative to each other about an axis extending through the pins. Alternatively, nubs can be integrally formed on the brackets or arms that can be received in corresponding receiving holes provided on either the arms or brackets, and this arrangement can likewise produce a hinged relationship. Tubular projections 146, similar to those of link and central components 110 and 120, extend from end 143 of section 142. Section 144 includes hollow tubes 152 and 154, with interior tube 152 nested within exterior tube 154, similar to those of link component 120. As can be seen, exterior tube 154 forms the periphery of section 144 and interior tube 152 extends from crossbar 156 that spans section 144. As with previously described link component 120, joint component 140 can be connected to another like joint component 140, or joint component 160, or link, spacer and central components 110, 120 and 180 in the manner previously described.

FIGS. 5A-5C show joint component 160 in greater detail. Joint component 160 is similarly formed of two sections 162 and 164 connected by a ball-and-socket joint, with ball 178 extending from section 162 and engaged in socket 176 of section 164. The ball-and-socket joint allows the two sections to pivotally move relative to each other in any direction. Tubular projections 166 (similar to those of link, joint and central components 110, 120 and 140) extend from section 162. Section 164 includes hollow tubes 172 and 174 with interior tube 174 nested within exterior tube 172 (similar to those of link component 120 and joint component 140). Exterior tube 172 forms the periphery of section 164 (similar to joint component 140). As with previously described link and joint components 120 and 140, joint component 160 can be connected to another like joint component 160, or joint component 140, or link, spacer and central components 110, 120 and 180 in the manner previously described.

Additional joint components are also contemplated, including but not limited to joint components that rely on flexible hinges between sections, such as those described in pending and commonly owned U.S. application Ser. No. 10/948,911 incorporated herein by reference in its entirety. Joint components that rely on two sections connected by flexible hinges will bend or flex around the flexure, rather than pivot. One of skill in the art will further appreciate that a wide variety of joints or joint systems known in the art will be applicable to the present invention.

Figure 6B:
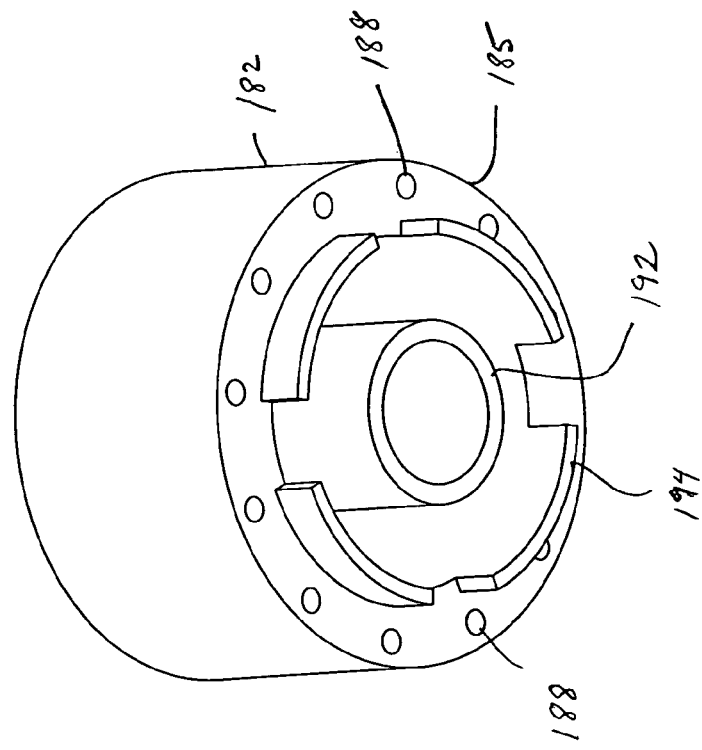
FIGS. 6A-6B are enlarged perspective views of a spacer component of the assembled articulating mechanism of FIG. 1.
Figure 6A:
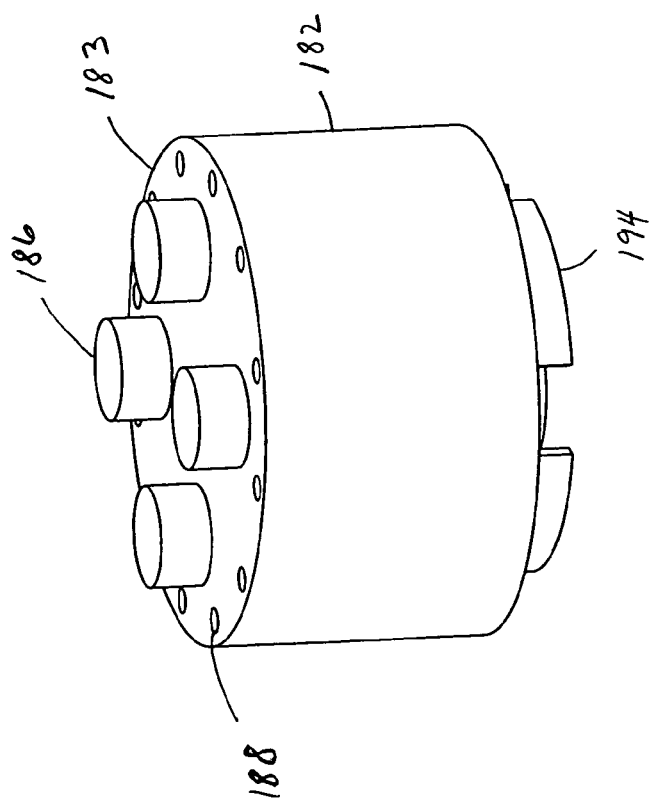
Figure 6D:
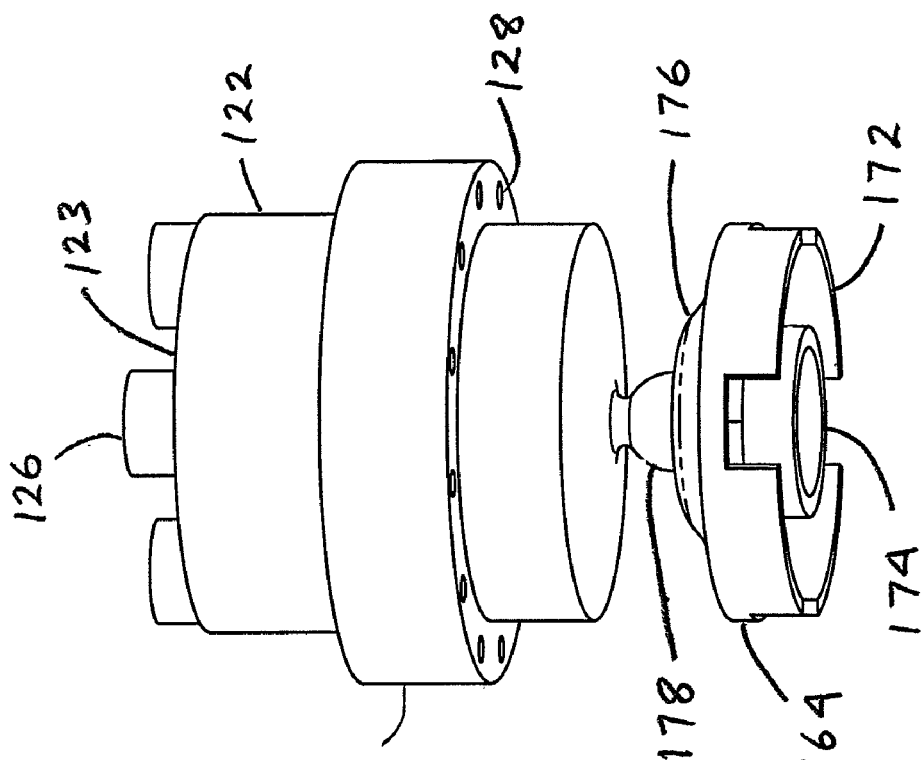
FIGS. 6C-6D are enlarged perspective views of an integrally formed link-joint component that may be used with the articulating mechanism of FIG. 1.
Figure 6C:
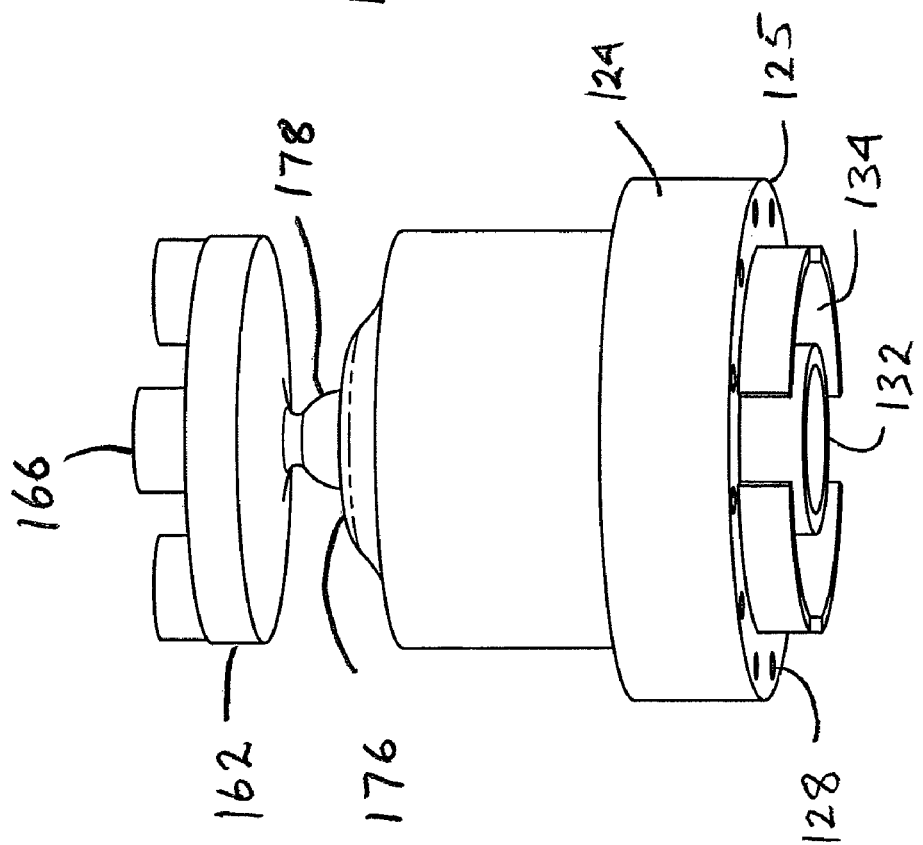

FIGS. 6A-6B show spacer component 180 in greater detail. Body 182 of spacer component 180 is generally cylindrical, with cable channels 188 positioned at a radial distance from the central axis of the component and that open to each end 183 and 185. Tubular projections 186 extend from end 183 of the spacer component (similar to central, link and joint components 110, 120, 140 and 160). Opposite end 185 includes hollow tubes 192 and 194, with interior tube 192 nested within exterior tube 194 (similar to link and join components 120, 140 and 160).

FIGS. 7A-7B show an alternative embodiment of cables that can be used in cables sets for connecting link components. FIG. 7A shows cable 202 which terminates at either end with narrower neck portions 201 and 203 and terminal caps 205 and 207. Cable stop 208, which is wider than cable channels on link components, include slot 209 and is configured to snap-fit onto the neck portions 201 and 203. Referring back to FIGS. 1A-1B, it can be appreciated how the cables connect link component pairs. Cables 202, 204, and 206 are of varying lengths and connect discrete pairs of link components 120 positioned on either side of central component 110. Each set of cables is threaded through cable channels of the central component and the one or more link components 120. A given cable is positioned to connect a pair of link components such that the neck portions 201 of cables extend out from the cable channels (in a direction away from the central component). Cable stops 208 are then snapped into place on the neck portions of the cables. Cable stops 208 can be further rotated such that slots 209 are oriented to face outwardly from the link components to avoid inadvertent removal of the stops.

In the assembled mechanism of FIG. 1A, each pair of connected link components is associated with discrete subassemblies of components located on either side of central component 110, thus also forming subassembly pairs 101 and 102, 103 and 104, and 105 and 106. Each subassembly includes at least one link component 120 and at least one joint component 140 or 160 that establish a link-joint unit. At least one pair of link components of subassembly pairs are connected by cables sets. The link and joint components of these subassemblies can either be directly connected to each other, or indirectly connected to each other, e.g., by the provision of one or more intervening spacer components. Numerous combinations of link, joint and optionally spacer components can form the subassembly pairs. As seen in FIG. 1A and more clearly in FIG. 1B, subassembly 102 is formed of ball-and-socket joint component 160, spacer component 180 and link component 120. Subassembly 104 is formed of two sequential hinge joint components 140 and link component 120. Subassembly 106 is formed of two hinge joint components 140 with intervening spacer component 180 and link component 120. Movement of any one subassembly pair is controlled by its corresponding cable set and is independent of any other subassembly pair. In certain variations, for example, a cable set will include three cables spaced 120 degrees apart, although other cable numbers and spacing configurations can be used.

Because ball-and-socket joint component 160 is pivotable in any direction, subassemblies that include ball-and-socket joint component 160, such as subassemblies 101 and 102, are moveable in three degrees freedom, i.e., including up/down motion, left/right motion, and rotational or "rolling" motion. Similar motion can be obtained by combining two (or more) hinged joint components 140 into a subassembly, such as in subassemblies 103, 104, 105 and 106. To achieve the greatest freedom of motion, at least one hinged joint component 140 is oriented orthogonal to at least one other hinged joint component 140, as in subassemblies 103, 104, 105 and 106. By using a set of at least three cables to connect a pair of such subassemblies, the subassembly pair can be manipulated or moved in three degrees of freedom, independently of any other subassembly pairs. In applications where a more limited freedom of motion is acceptable, the hinged joint components need not be orthogonal. In such applications, configurations where two or more hinged joint components 140 are oriented parallel to each other or are offset from each other anywhere from 0-90 degrees, can be utilized. Or a single hinge joint component 140 can be used, providing movement in a single degree of freedom.

For the assembled articulating mechanism of FIG. 1A, the cables fixed to a proximal subassembly of a given pair travel directly through central component 110 to connect with a corresponding distal subassembly of the pair. More particularly at least one pair of link components of the proximal and distal subassembly is connected by a cables set, as has been noted. Movement of active links or link-joint units in the proximal subassemblies results in inverted, reciprocal movement of distal subassemblies through the active links or link-joint units of the distal subassemblies. In other variations of the central component, as previously noted, the cables can be twisted or rotated 180 degrees while running through the central component so that the reciprocal movement at the distal end is mirrored. The assembled articulating mechanisms of the invention may be configured to include cables twisted in any amount between 0 degrees to 360 degrees to provide for 360 degree range of reciprocal motion. The mechanism components, including e.g. the central component, can be modified as will be apparent to one of skill in the art in order to accommodate such twisting, for example, by constructing the components in a tubular fashion that allow the cables to be twisted as they pass through the component.

In the assembled mechanism of FIGS. 1A-1B, there is a one to one, or symmetrical, correspondence of components for each pair of subassemblies. This is not always necessary and there may be applications where it is desirable for a subassembly pair or pairs to have asymmetrical arrangements of components. For example, additional spacer components can be added to one subassembly of the pair, which can be desirable for providing additional length to the proximal and/or distal end of the mechanism. In addition the inclusion of additional (or a greater relative number of) of spacer components at one end of the assembled mechanism allows for the proportional scaling of movement or motion of the corresponding other end. For example, the inclusion of additional spacer components (or a greater relative number of spacer components) at the proximal end would require a more exaggerated movement by the user at the proximal end to achieve the desired motion at the distal end. This could be advantageous in situations where fine, delicate controlled movements were desired, such as, for example, situations where there is a risk that a user may not possess the necessary dexterity to perform the desired procedure absent such proportional scaling of the distal end movement or motion. Alternatively, additional spacer components (or a greater relative number of spacer components) could be provided on the distal end, in which case the degree of distal end movements would be proportionally greater than those of the proximal end, which may also be desirable for particular applications. In addition to the above, proportional scaling of movement or motion can also be accomplished by increasing or decreasing the cable channel pattern radius of the link or spacer components, at either the proximal or distal end, as is described e.g. in pending and commonly owned U.S. application Ser. Nos. 10/948,911 and 10/928,479 incorporated herein by reference in their entireties. Adjusting cable bias, i.e., providing for neutral, positive, or negative cable bias, can also be accomplished by altering the configuration of cable channels in a link-joint unit, as is described in U.S. application Ser. Nos. 10/948,911 and 10/928,479 incorporated herein by reference in their entireties.

Although the assembled articulating mechanism of FIGS. 1A-1B has been illustrated as having a certain number of components and subassemblies, this is solely for the illustrative purpose of indicating the relationship of the components and subassemblies to one another. Any number of components and subassemblies may be employed, depending on such factors as the intended use and desired length of the assembled articulating mechanism. Further, while certain embodiments of link, joint, spacer and central components are exemplified herein, the components, systems, and assembled mechanisms of the invention are not so limited. For example, the link and joint components can incorporate the pivoting or bending features and characteristics of a variety of known link systems and link systems such as described in U.S. application Ser. Nos. 10/444,769, 10/928,479, 10/948,911, and 10/997,372 incorporated herein by reference. In addition, any or all of the components can be further provided with channels that allow for the passage of wires, other cables, fiber optics, etc., that may be connected to or involved in controlling a tool or other element deployed at one end or the other of the mechanism, such as is described in U.S. application Ser. Nos. 10/444,769, 10/928,479, 10/948,911, and 10/997,372. Further, while link, joint, spacer and central components have generally been described herein separately, it will be appreciated that various features of one or more such components can be integrally formed into a single component. For example, a link-joint unit (such as shown in FIGS. 6C and 6D, for example) or a spacer-joint unit can be integrally formed.

As shown in FIG. 1A, different cables of varying lengths, i.e., cables 202, 204 and 206 can be provided to assemble the desired articulating mechanism. In addition, cable extenders 210, as depicted in FIGS. 8A-8B can also be provided to extend the length of a given cable 202, 204, and 206 in order to provide cables of varying overall lengths. The provision of cable extenders provides even greater flexibility in assembling articulating mechanisms of varying dimensions above and beyond those that can be formed based on a finite set of cables of predetermined length. Cable extender 210 is of the same diameter as cables 202, 204 and 206 and has a similar neck portion 211 and terminal cap 215 at one end. The other end includes slot 213 and cut-out 217 that are configured to receive and retain neck portion and terminal cap of cables 202, 204 or 206, or of another cable extender 210. Cable stop 208 similarly snaps onto neck portion 211 to secure to cable extend 210 against a link component in an assembled mechanism. As a precaution, the cable stop can be rotated such that slot 209 is oriented away from the link component to further avoid inadvertent removal of the stop.

FIGS. 9A-D show an alternative embodiment of a cable, cable extender, and cable stop system than can be similarly employed to assemble mechanisms according to the invention. Cable 222 as shown terminates in threaded ends 221 and 223. Cable stop 228 is reciprocally threaded on its interior and can be threadably engaged with ends 221 and 223 to secure the cable against a link component. Cable extender 230 can be used to extend the length of cable 222. Cable extender 230 has one threaded end 231 and the other end has an internally threaded bore 233 that receives threaded ends 221 or 223 of cable 232 or the threaded end 231 of another cable extender 230 (as shown in FIG. 9D). Cable 222 thus acts as a starter cable which can then be extended in either direction. When the cables of this system are used to connect link components in an assembled mechanism, the overall effective tension of any given connecting cable can be adjusted by loosening or tightening the cable stop 228 threaded onto the cable end and thus increase or decrease the tension or slack in a given cable which aides in e.g., accommodating varying tolerances of components. In further embodiments, cables or cable extenders can be directly threaded into mechanism components that have reciprocal internally threaded bores. Additional methods for connecting cable extenders to cables and cables to cable stops will be apparent to one of skill in the art. For example the cable stop can incorporate the head shape of a conventional cable tie or beaded tie, with indentations or beads on the cable engaging the head to connect the cable to the link or other component. In other cases, the cable can be secured to a cable stop or link or other component by bonding or gluing the cable to the cable stop or link or other component or within the cable channels themselves. In this case the bond could be broken or the cable cut to release and disassemble the formed mechanism. In all cases, the cable stops can be attached to or integrally formed with the link or other component.

In order to provide the greatest degree of flexibility, the link, joint and spacer components of a given system may be sized to a single length standard and the corresponding initial starter cable and cable extenders will be proportionally sized relative to the component standard. The central component can be sized to a multiple of the link, joint and spacer standard. In such a system, numerous configurations of components are possible, and for each configuration, appropriate length cables can be assembled to connect link component pairs.

FIGS. 10A-10C show another embodiment of a central component according to the invention that is configured to adjust the tension of all the cables of an assembled mechanism. Central component 310 includes first and second sections 312 and 314. Section 312 includes left-handed thread section 317 and section 314 includes right-handed thread section 319. The sections are threaded onto central nut 320. Sections 312 and 314 further include tubular projections 316 extending from ends 313 and 315 of sections 312 and 314, respectively, similar to those of central component 110, such that central component 310 can likewise engage with link, joint and spacer components 120, 140, 160 and 180. Cable channels 318 are similarly provided for receipt and passage of connecting cables. When incorporated into an assembled mechanism, rotation of nut 320 relative to sections 312 and 314 causes translation of sections to either increase or decrease the length of component 310, which in turn either increases or decreases the tension of the connected cables sets as a whole. Sections 312 and 314 can further be configured to resist rotation relative to each other, for example, by a reciprocal boss and socket interface on the opposing ends of the threaded sections. Such a configuration will avoid putting undue twisting force onto the assembled cables while nut 320 is rotated.

The central component in general provides flexibility to the system. By providing central components of differing lengths, the resultant assembled mechanisms can have their corresponding joint, link and/or spacer component pairs spaced farther apart or closer together. Central components also provide for easier assembly of resultant mechanisms in situations where the central component and the joint, link and/or spacer component are releasably connectable to one another, as the central component can be the starting point for attachment of subsequent components. However, it will also be appreciated that articulating mechanisms can be assembled without a central component, as long as at least two link-joint components are assembled that are oriented opposite to one another.

Figure 11B:
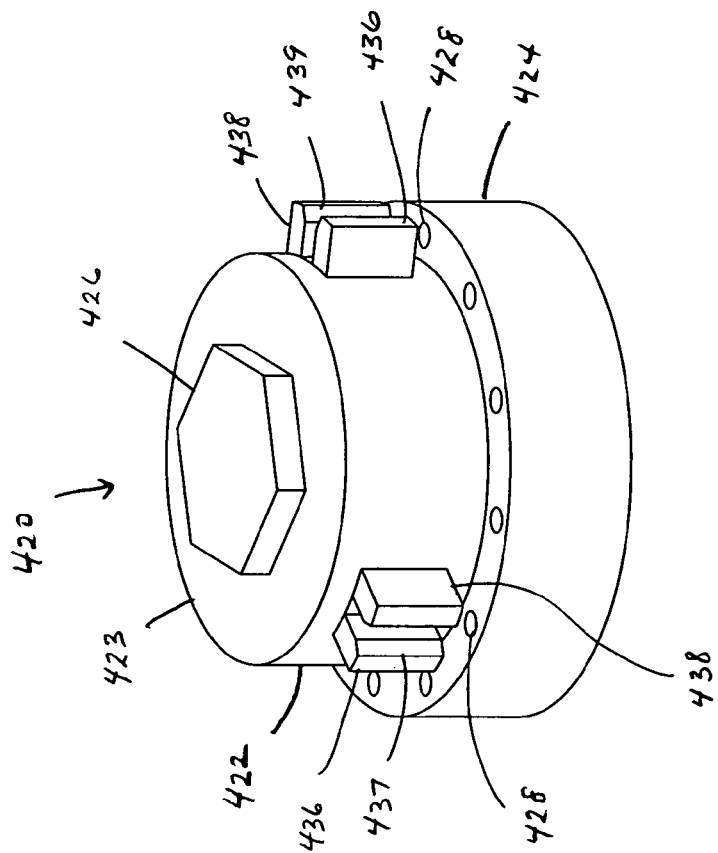
FIGS. 11A-11B are perspective views of a link component according to another embodiment of the invention.
Figure 11A:
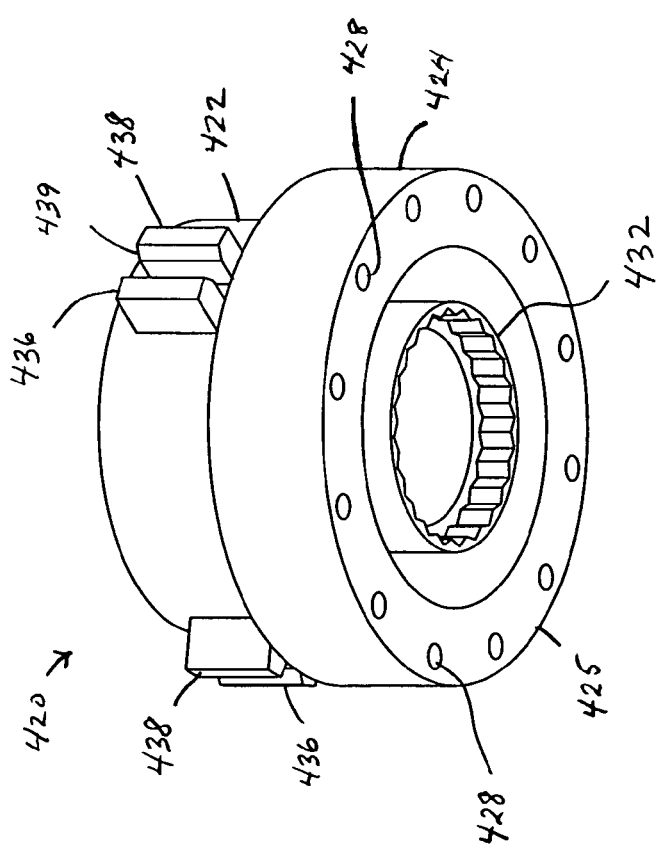

FIGS. 11A-11B depict another embodiment of a link component according to the invention. Link component 420 is similar to link component 120 in certain aspects. Like link component 120, link component 420, similarly includes body 422 that is generally cylindrical with rim section 424 extending radially outward from body 422. Rim section 424 includes cable channels 428 that extend through the rim section for receiving cable sets. Instead of an interlocking tubular system, link component 420 instead has hex boss 426 that extends from end 423 and that is configured for receipt in recessed socket 432 of opposite end 425 of another link component 420. Similar hex bosses and sockets can be provided on central, joint and spacer components such that the components are compatible for assembling together. Alternative geometric boss and socket patterns can also be employed. In such a system, the tension provided by connecting cables upon assembly keep the components in contact with one another. Alternatively, the components could be easily converted to releasably connect to one another, e.g. by configuring the boss to be slightly oversized and providing stress-relief cuts to the socket walls. This would provide for a snap-fit connection between the components. Link component 420 further includes a cable anchor formed by tines 436 and 438 extending radially from body 422. Tines 436 and 438 are positioned to bracket a cable channel such that a cable emerging from the cable channels can be pressed between the tines and secure the cable to the link component. The tines include chamfers 437, 439 to aid in guiding the cable between the tines. FIGS. 12A-12B in particular detail how cable 402 can be threaded through channel 428 and then press fit in between tines 436 and 438 to secure the cable to the link component. The tension or slack imparted to the cable can thus be individually controlled. Additional tines in varying orientations can be further provided for additional security. Link component 420 envisions three sets of tines positioned to secure three separate cables, but numerous different arrangements of tines and corresponding cable channels are contemplated as will be apparent to one of skill in the art. As can also be seen, socket 432 is configured to receive another component with a hex boss rotated in various degrees relative to the first link component 420. This allows the link components to be aligned relative to each other in an assembled mechanism such that a set of tines on a given link component can secure a cable while other link components in the same assembly are positioned such that the secured cable passes through channels that are not associated with tines.

Figure 13B:
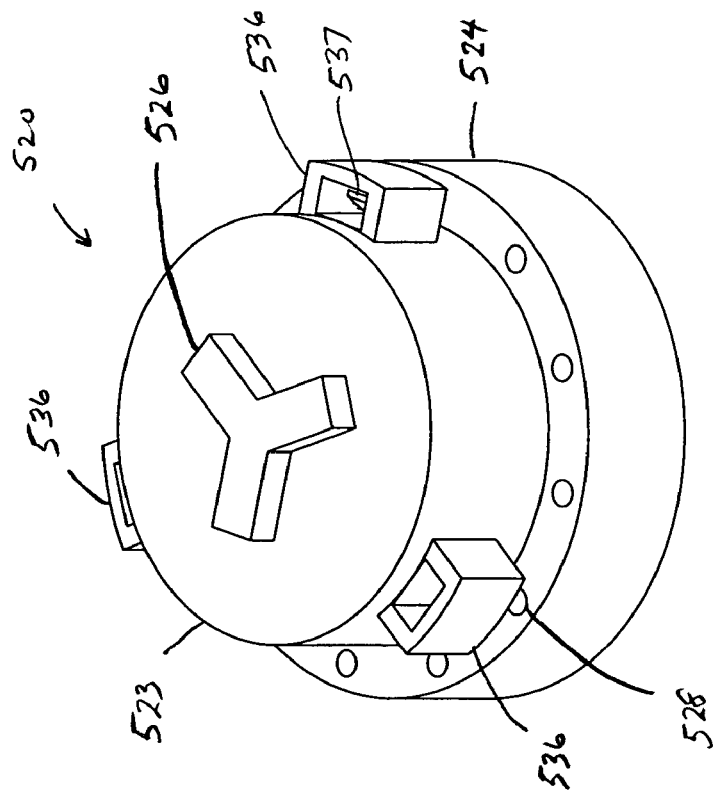
FIGS. 13A-13C are perspective views of a link component according to yet another embodiment of the invention.
Figure 13A:
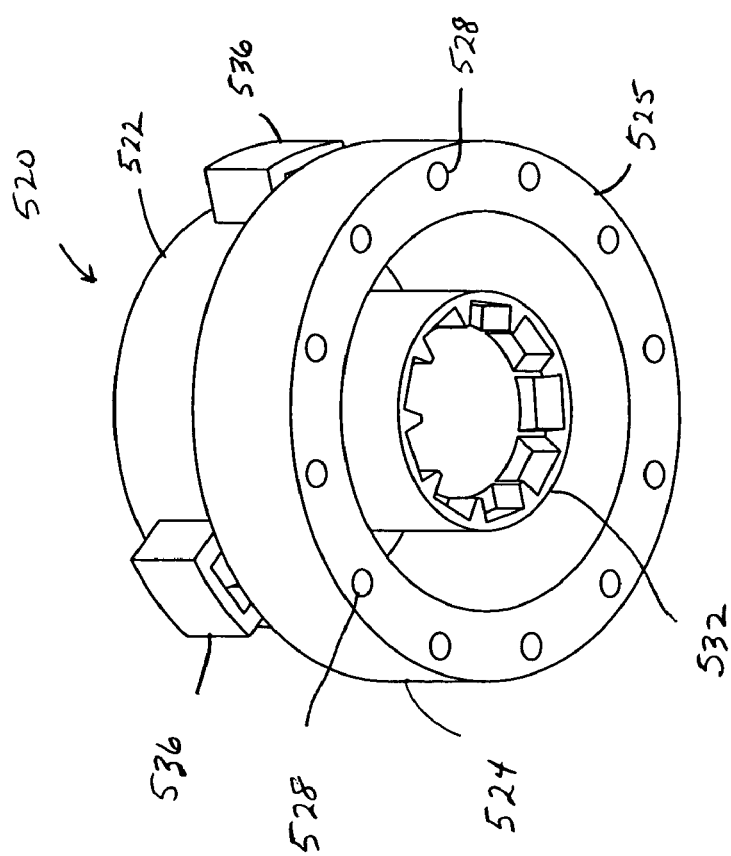
Figure 13C:
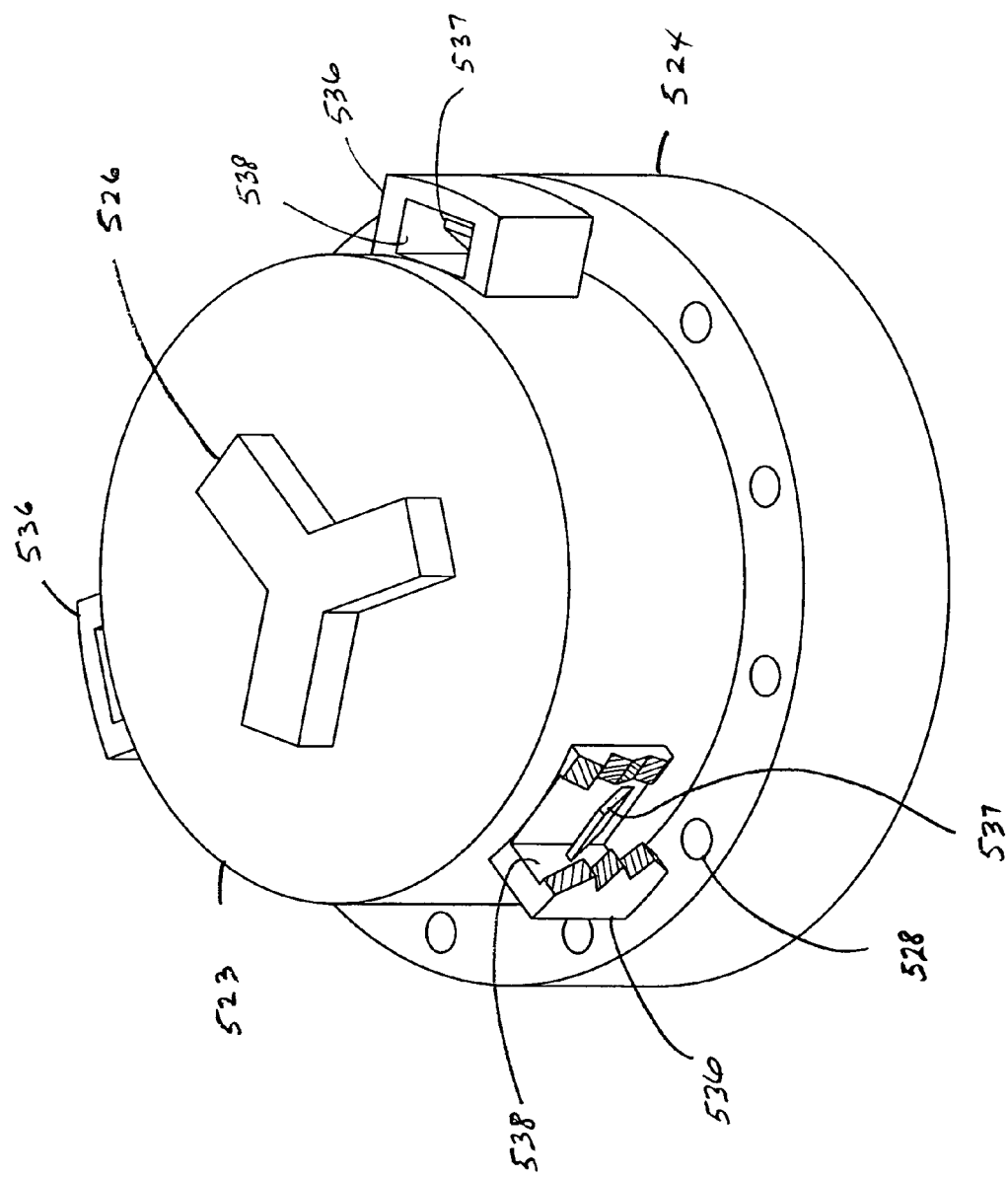

FIGS. 13A-13C depict another embodiment of a link component according to the invention. Link component 520 includes body 522 that is again generally cylindrical with rim section 524 extending radially outward from body 522. Rim section 524 includes cable channels 528 that extend through the rim section for receiving cable sets. Y-shaped boss 526 extends from end 523 and is configured for receipt in recessed socket 532 of opposite end 525 of a second link component 520. Again, similar Y-shaped bosses and corresponding sockets can be provided on compatible central, joint and spacer components. As can also be appreciated, the socket will receive a Y-shaped boss rotated in various degrees relative to the orientation of Y-shaped boss of the link component. The Y-shaped bosses and corresponding sockets can be configured to releasably connect or simply abut. Link component 520 further includes cable anchors formed by guide brackets 536 extending radially from body 522, and that define a guide channel 538 surrounded by bracket 536 and the exterior wall of body 522. The guide brackets 536 are positioned to bracket cable channels 528 such that a cable emerging from the cable channel can be received through guide channel 538. Prong 537 located within guide channel 538 extends from the exterior wall of body 522 in an angled direction away from the cable channel 528. Prong 537 deflects to allow passage of cable through guide channel 538 in the direction away from cable channel 528 but engages such a cable and resists movement of the cable in the opposite direction. Link component 520 shows three brackets 536 positioned to secure three separate cables, but again as will be apparent to one of skill in the art numerous different arrangements of brackets and corresponding cable channels are contemplated. In an assembled mechanism the bracket guides on a given link component can secure a cable while other link components in the same assembly are positioned such that the secured cable passes through channels that are not associated with bracket guides. To disassemble a mechanism using such a link component, the prongs can simply be depressed in order to release the cables. One skilled in the art can appreciate that there are many other methods of quickly securing and releasing cables to link components include e.g. the provision of one or more pivoting cleats or cam-cleats on the link components that receive and secure the cables. Still other methods of securing the cable to a link component include providing similar guide brackets with set screws that can threaded through bracket to press the cable against the component.

Link component 620 shown in FIGS. 14A-14C are similar to link component 520 but are formed of two separate parts that allow for greater convenience in positioning the guide brackets relative to the desired cable channels and also provide an ease of manufacture. Link component 620 includes body 622 and rim section 624 extending radially outward from the body, with cable channels 628 that extend through the rim section for receiving cable sets. Body 622 further includes a series of longitudinally extending grooves 633 located around the periphery of body 622. Ring 634 fits over body 622 and includes tongues 635 extending interiorly of the ring and that fit grooves 633. The tongue-groove fit locks the ring in place relative to body 622. On the exterior of ring 634 are cable anchors formed by guide brackets 636 similar to guide brackets 536. Each guide bracket defines a guide channel 638 for receiving a cable and includes prong 637 located within guide channel 638 and extending from the exterior wall of ring 634. The ring 634 is fitted onto the body 622 such the prong is an angled direction away from the cable channel 628 and operates to retain a cable passing through the guide channel in the same as previously described. Ring 634 could alternatively include tines, cleats or any other quick-connect method known in the art in place of guide brackets 636.

As previously noted, the components of the present invention can be readily assembled to create customized articulating mechanisms of a variety of lengths and characteristics. Further, by providing for releasable connections of the connecting cables, such mechanisms can be both quickly and easily assembled and disassembled. For components designed to releasably connect to one another, the components can first be connected together in the desired configuration and then the associated cables for each link component pair can be threaded through the connected components and secured against the link components of each pair to operably connect the pair. Alternatively, where components are designed to simply abut or interfit with one another, it may be easier to simply secure a cable or set of cables to an end link component and then string the additional components onto the cables, adding new cables or cable sets when adding a new link component. Once all the components are strung onto the cables, the cables can be further secured and tensioned against the link components in the various manners described. The provision of cable anchors integrally formed into link components for releasably securing and tensioning the cables further aids in easy assembly.

Components that are releasably connectable to one another have the advantage of being able to confer torque along a mechanism assembled from such components. Other methods of conferring torque are also available, for example, components that abut one another in a slip fit arrangement can confer torque, as can components that include bosses and reciprocal sockets, such as those depicted in FIGS. 11-14. Other methods include modifying the links to include torque conferring features, such as those described in, e.g., in U.S. application Ser. Nos. 10/948,911, and 10/997,372 incorporated herein by reference.

Consistent with the above considerations, the link, joint, spacer and central components may further be of any size and shape, as the purpose dictates. For surgical applications, the size and shape of links usually depends on such factors as patient age, anatomy of the region of interest, intended application, and surgeon preference. The components are generally, but need not be, cylindrical, and as previously mentioned, central, link and spacer components may include channels for passage of the cables that connect link component pairs. The components can further be provided with additional channels for passage of additional cables, wires, fiberoptics or other like elements associated with a desired tool or instrument used in conjunction with the assembled mechanism. The cable channel diameters or widths, in the case of non-circular channels, are usually slightly larger than the cable diameters, creating a slip fit. The components may typically have a diameter from about 0.5 mm to about 15 mm or more depending on the application. For endoscopic/laparoscopic applications, representative diameters may range from about 2 mm to about 3 mm for small endoscopic/laparoscopic instruments, about 5 mm to about 7 mm for mid-sized endoscopic/laparoscopic instruments, and about 10 mm to about 15 mm for large endoscopic/laparoscopic instruments. For catheter applications, the diameter may range from about 1 mm to about 5 mm. Overall length of the components will vary, usually depending on the bend radius desired between components. Industrial, military, consumer, education, recreation, or toy uses may warrant larger sizes.

The various components may be formed of a number of materials known in the art and that can vary according to the application. For ease of manufacture, injection moldable polymers can be used including, e.g., polyethylene or copolymers thereof, polyethylene terephthalate or copolymers thereof, nylon, silicone, polyurethanes, fluoropolymers, poly(vinylchloride); and combinations thereof, or other suitable materials known in the art.

For surgical applications a lubricious coating may be placed on the components if desired to facilitate advancement of the assembled articulating mechanism. The lubricious coating may include hydrophilic polymers such as polyvinylpyrrolidone, fluoropolymers such as tetrafluoroethylene, or silicones. A radioopaque marker may also be included on one or more components to indicate the location of the assembled articulating mechanism upon radiographic imaging. Usually, the marker will be detected by fluoroscopy.

Cable diameters vary according to the application. For surgical applications in general, cable diameters and may range from about 0.15 mm to about 3 mm. For catheter applications, a representative diameter may range from about 0.15 mm to about 0.75 mm. For endoscopic/laparoscopic applications, a representative diameter may range from about 0.5 mm to about 3 mm.

Cable flexibility may be varied, for instance, by the type and weave of cable materials or by physical or chemical treatments. Usually, cable stiffness or flexibility will be modified according to that required by the intended application of the articulating mechanism. The cables may be individual or multi-stranded wires made from material, including but not limited to biocompatible materials such as nickel-titanium alloy, stainless steel or any of its alloys, superelastic alloys, carbon fibers, polymers, e.g., poly(vinylchloride), polyoxyethylene, polyethylene terephthalate and other polyesters, polyolefin, polypropylene, and copolymers thereof; nylon; silk; and combinations thereof, or other suitable materials known in the art. In certain applications, cables can be formed of conventional cord, string or thread.

The natural configuration of the assembled articulating mechanisms is usually linear. If maintenance of a certain curvature or other complex configuration is desired at the distal end of the assembled articulating mechanism, the mechanism can be "locked" into place according to ways described e.g. in pending and co-owned U.S. application Ser. Nos. 10/444,769, 10/928,479, and 10/948,911, incorporated herein by reference in their entirety.

What is claimed as new and desired to be protected by Letters Patent of the United States is:

1. An articulating mechanism comprising:
    two or more link components, each link component including channels;
    two or more joint components, each joint component being capable of pivoting or flexing movement;
    link-joint units formed by the link components connected to the joint components; one or more cables releasably secured against the link component of one link-joint unit;
    a central component disposed between two of the link-joint units and the central component is configured to expand or contract along its length;
    a connected link component pair formed by two of the link-joint units, such that movement of one link component of the pair causes relative movement of the other link component of the pair directly through movement of the one or more cables interconnecting the two link components; and
    a cable stop, abutting at least one of the link-joint units and configured to be releasably secured to the one or more cables.

2. The articulating mechanism of claim 1 wherein the link, joint and central component are releasably connected together.

3. The articulating mechanism of claim 1 further comprising one or more spacer components.

4. The articulating mechanism of claim 3 wherein the spacer, link, and joint components are releasably connected together.

5. The articulating mechanism of claim 1 wherein the central component further comprises first and second sections with threaded portions and a central nut having reciprocally threaded portions engaged therewith.

6. The articulating mechanism of claim 1 further comprising one or more cable stops releasably secured to the terminal ends of one or more cables.

7. The articulating mechanism of claim 1 wherein the cables further comprise multiple cable segments connected together.

8. The articulating mechanism of claim 1 wherein the link component further include a cable anchor that releasably secures one or more cables.

9. The articulating mechanism of claim 8 where the cable anchor secures the one or more cables by a press-fit.

10. The articulating mechanism of claim 8 wherein the cable anchor allows movement of the cables in one direction while restricting movement of the cables in the opposite direction.

11. The articulating mechanism of claim 8 wherein the cable anchor is threaded to accommodate a reciprocally threaded cable.

12. The articulating mechanism of claim 1 wherein the link component and the joint component of at least one of the link-joint units are integrally formed as a single piece.

13. An articulating mechanism comprising:
   two or more link components, each link component including channels;
   two or more joint components, each joint component being capable of pivoting or flexing movement;
   link-joint units formed by the link components connected to the joint components;
   one or more cables releasably secured against the link component of one link-joint unit;
   a central component disposed between two of the link-joint units and the central component is configured to expand or contract along its length;
   a connected link component pair formed by two of the link-joint units, such that movement of one link component of the pair causes relative movement of the other link component of the pair directly through movement of the one or more cables interconnecting the two link components; and
   a cable stop, with a snap-fit connection, abutting at least one of the link-joint units and configured to releasably abut the link component and be kept in contact from tension provided by the one or more cables.

14. The articulating mechanism of claim 13 wherein the at least one link-joint unit and the cable stop each have either a geometric boss or a corresponding socket.

15. The articulating mechanism of claim 13 wherein the link, joint and central component are releasably connected together.

16. The articulating mechanism of claim 13 further comprising one or more spacer components.

17. The articulating mechanism of claim 16 wherein the spacer, link, and joint components are releasably connected together.

18. The articulating mechanism of claim 13 wherein the central component further comprises first and second sections with threaded portions and a central nut having reciprocally threaded portions engaged therewith.

19. The articulating mechanism of claim 13 further comprising one or more cable stops releasably secured to the terminal ends of one or more cables.

20. The articulating mechanism of claim 13 wherein the cables further comprise multiple cable segments connected together.

21. The articulating mechanism of claim 13 wherein the link component includes a cable anchor that releasably secures one or more cables.

* * * * *